(12) United States Patent
Cantley et al.

(10) Patent No.: US 12,296,164 B2
(45) Date of Patent: May 13, 2025

(54) TARGETED CUE DELIVERY SYSTEM FOR GAIT REGULATION

(71) Applicant: Oxford University Innovation Limited, Botley (GB)

(72) Inventors: James Cantley, Botley (GB); Dongli Li, Botley (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 17/769,016

(22) PCT Filed: Oct. 22, 2020

(86) PCT No.: PCT/GB2020/052665
§ 371 (c)(1),
(2) Date: Apr. 14, 2022

(87) PCT Pub. No.: WO2021/079127
PCT Pub. Date: Apr. 29, 2021

(65) Prior Publication Data
US 2024/0100328 A1    Mar. 28, 2024

(30) Foreign Application Priority Data
Oct. 22, 2019 (GB) ..................... 1915235

(51) Int. Cl.
*A61N 1/36* (2006.01)
*A61B 5/00* (2006.01)
(Continued)

(52) U.S. Cl.
CPC .......... *A61N 1/36003* (2013.01); *A61B 5/112* (2013.01); *A61B 5/1121* (2013.01);
(Continued)

(58) Field of Classification Search
CPC ............ A61N 1/36003; A61N 1/36031; A61B 5/112; A61B 5/1121; A61B 5/4836;
(Continued)

(56) References Cited

U.S. PATENT DOCUMENTS

2014/0303508 A1* 10/2014 Plotnik-Peleg ........ A61B 5/112
600/595
2018/0126158 A1* 5/2018 Perez ................... A61B 5/1116
(Continued)

FOREIGN PATENT DOCUMENTS

CN      106 377 837 A    2/2017
JP      2016150178 A     8/2016
(Continued)

OTHER PUBLICATIONS

International Search Report and Written Opinion for WO 2021/079127 (PCT/GB2020/052665), dated Jan. 20, 2021, pp. 1-10.
UK Search Report for GB 1915235.4, dated Apr. 17, 2020, pp. 1-3.

*Primary Examiner* — Catherine M Voorhees
(74) *Attorney, Agent, or Firm* — Thomas |Horstemeyer, LLP

(57) ABSTRACT

Embodiments of the present invention provide a system (100) for providing targeted cue delivery to regulate a gait of a user comprising a first cue delivery device (131) configured to provide somatosensory stimulation to a first leg of the user, a second cue delivery device (132) configured to provide somatosensory stimulation to a second leg of the user, one or more inertial sensors (121, 122) configured to output movement data indicative of the gait of the user, and a controller (110) configured to receive the movement data from the one or more inertial sensors (121, 122), determine a cue pattern for each of the first and second cue delivery devices (131, 132) independence on the movement data, and output a respective control signal (135, 136) to
(Continued)

control each of the first and second cue delivery devices (135, 136) to provide stimulation according to the cue pattern.

19 Claims, 15 Drawing Sheets

(51) Int. Cl.
  *A61B 5/11* (2006.01)
  *G16H 10/60* (2018.01)
(52) U.S. Cl.
  CPC ........ *A61B 5/4836* (2013.01); *A61N 1/36031* (2017.08); *G16H 10/60* (2018.01)
(58) Field of Classification Search
  CPC ........ A61B 2505/09; A61B 2562/0219; A61B 5/4082; A61B 5/6828; G16H 10/60; A61H 23/02
  See application file for complete search history.

(56) References Cited

U.S. PATENT DOCUMENTS

| | | | |
|---|---|---|---|
| 2018/0132757 A1* | 5/2018 | Kong | A61B 5/1118 |
| 2018/0318583 A1* | 11/2018 | McBride | A61B 5/112 |
| 2019/0105217 A1* | 4/2019 | Prattichizzo | A61H 3/00 |
| 2019/0336040 A1* | 11/2019 | Chang | A61B 5/1038 |
| 2020/0382286 A1* | 12/2020 | Akamandor | H04W 12/033 |

FOREIGN PATENT DOCUMENTS

| | | | | |
|---|---|---|---|---|
| KR | 20170004380 A | 1/2017 | | |
| WO | WO-2010039674 A2 * | 4/2010 | | A61B 5/112 |
| WO | 2015/164456 A2 | 10/2015 | | |
| WO | 2017/023864 A1 | 2/2017 | | |
| WO | 2017/060132 A1 | 4/2017 | | |
| WO | 2017/199171 A1 | 11/2017 | | |
| WO | 2019/144869 A1 | 8/2019 | | |

* cited by examiner (a) walking without intervention (b) walking with the somatosensory responsive cueing

TARGETED CUE DELIVERY SYSTEM FOR GAIT REGULATION

CROSS-REFERENCE TO RELATED APPLICATIONS

This application is the National Stage of International Application No. PCT/GB2020/052665, filed Oct. 22, 2020, which claims priority to GB 1915235.4. filed Oct. 22, 2019, which are entirely incorporated herein by reference.

BACKGROUND

The present invention relates to targeted cue delivery for gait regulation. Specifically, the invention relates to a system and a method for providing targeted cue delivery to regulate the gait of a user.

A user may routinely experience a number of abnormal gait events, for example Freezing of Gait (FoG) or festination events associated with Parkinson's Disease (PD) which may be highly disruptive. The user may find difficulty in resuming normal gait following the onset of an abnormal gait event. It may therefore be desired to regulate or assist the gait of a user routinely exhibiting these various abnormal gait events. The user may require assistance resuming normal gait following the onset of an abnormal gait event, or regulation of gait to prevent the onset of an abnormal gait event.

The regulation may be performed by the provision of cues to prompt the user to resume walking normally following the onset of an abnormal gait event. However, existing solutions, for example audible prompting, may not effectively aid the user to resume normal gait. Furthermore, abnormal gait events may be inaccurately identified or predicted.

It is an object of embodiments of the invention to at least mitigate one or more of the problems of the prior art.

SUMMARY OF THE INVENTION

Embodiments of the invention comprise a system and a method as set forth in the appended claims.

According to an aspect of the invention there is provided a system for providing targeted cue delivery to regulate a gait of a user comprising: a cue delivery device configured to provide somatosensory stimulation to a leg of the user; one or more inertial sensors configured to output movement data indicative of the gait of the user; and a controller configured to receive the movement data from the one or more inertial sensors; determine a cue pattern for the cue delivery device in dependence on the movement data, and output a control signal to control the cue delivery devices to provide stimulation according to the cue pattern.

According to another aspect of the invention there is provided a system for providing targeted cue delivery to regulate a gait of a user comprising: a first cue delivery device configured to provide somatosensory stimulation to a first leg of the user; a second cue delivery device configured to provide somatosensory stimulation to a second leg of the user; one or more inertial sensors configured to output movement data indicative of the gait of the user; and a controller. The controller is configured to receive the movement data from the one or more inertial sensors; determine a cue pattern for each of the first and second cue delivery devices in dependence on the movement data, and output a respective control signal to control each of the first and second cue delivery devices to provide stimulation according to the cue pattern.

Optionally, the controller is configured to extract one or more gait characteristics from the movement data; and determine the cue pattern for each of the first and second cue delivery devices in dependence on whether one or more of the gait characteristics meet one or more of a first set of predetermined criteria.

The controller may be configured to determine an intensity of stimulation in dependence on a level of abnormality of the gait characteristics.

The controller may optionally be configured to control the first and second cue delivery devices to cease from providing stimulation or reduce an intensity of the stimulation to the user if one or more of a second set of predetermined criteria are not met. If the first set of predetermined criteria are not met at any point, optionally no control signal is output to the cue delivery devices.

The first set of predetermined criteria may comprise a threshold between normal and abnormal gait characteristics. Optionally, the first set of predetermined criteria may be substantially the same as the second set of predetermined criteria.

Optionally, the gait characteristics comprise an indication of one or both of a pace of the user and a stride length of a user, and the predetermined criteria comprise one or both of a minimum or maximum pace threshold and a minimum or maximum stride length threshold. The gait characteristics may comprise an indication of a step symmetry of the user, and the predetermined criteria may comprise a threshold value of step symmetry, for example a minimum or maximum value.

The controller may be configured to determine one or more predetermined criteria in dependence on historic movement data associated with the user, for example the minimum or maximum pace threshold, the minimum or maximum stride length threshold, or the minimum or maximum gait symmetry threshold. The historic movement data may comprise an indication of fall frequency, and the controller may be configured to determine one or more predetermined criteria, for example the maximum pace threshold, further in dependence on the indication of fall frequency.

Optionally, the controller is configured to determine the cue pattern to be intermittent stimulation by one or both cue delivery devices at a rhythm corresponding to an appropriate pace for the user. The appropriate pace may be predetermined, i.e. a pre-set rhythm.

The controller may be configured to determine the appropriate pace for the user in dependence on historic movement data associated with the user, for example the user's average pace throughout a portion of the historic movement data. Pace is taken to mean the step frequency of the user.

Optionally, the gait characteristics comprise one or more characteristics of the movement data associated with a freezing of gait (FOG) event or a festination event. The movement data may comprise a plurality of frequency bands each corresponding to a range of frequency of movement. The gait characteristics may comprise one or more of a power of a first frequency band of the movement data associated with walking, a power of a second frequency band of the movement data associated with freezing of gait, a ratio of the power of the first and second frequency bands (freeze index), entropy of the movement data, and one or more wavelet transform features of the movement data.

The controller may be configured to associate the extracted gait characteristics with a likelihood of one of a freezing of gait (FOG) event or a festination, and the one or more predetermined criteria comprise a likelihood threshold.

The controller may be configured to apply a decision tree to the extracted gait characteristics; and associate the gait characteristics with a likelihood of being indicative of a freezing of gait (FOG) or festination event in dependence on the decision tree or a plurality of decision trees. The decision tree(s) may comprise a random forest classifier, support vector machine (SVM) or neural network. The controller may be configured to train the decision tree on historic movement data associated with the user indicative of at least one freezing of gait (FOG) or festination event and at least one period of normal gait.

Optionally the controller may be configured to determine the cue pattern to comprise unilateral stimulation for the first leg by the first cue delivery device; receive further movement data from the one or more inertial sensors; detect a step being taken by the first leg in the further movement data; and responsive to the step being taken, output a control signal to swap the unilateral stimulation from the first cue delivery device to the second cue delivery device.

The controller may optionally be configured to identify whether a normal walking pattern has been resumed, and if a normal walking pattern has been resumed, control each of the first and second cue delivery devices to cease providing stimulation. A normal walking pattern may be identified based on whether one or more gait characteristics are within a normal range.

Optionally, the inertial sensors comprise at least one gyroscope and/or at least one accelerometer. The inertial sensors may comprise at least two accelerometers, each configured to attach to a respective lower leg. The inertial sensors may comprise at least two gyroscopes, each configured to attach to a respective lower leg.

The controller may optionally be configured to receive first historic movement data associated with the provision of a first cue pattern to the user; receive second historic movement data associated with the provision of a second cue pattern to the user; and determine the cue pattern in dependence on a comparison between the first historic movement data and the second historic movement data.

Optionally, the controller is configured to associate a first time period with a first set of predetermined criteria and a second time period with a second set of predetermined criteria; determine whether a current time period corresponds to the first time period or the second time period; and selectively use the predetermined criteria associated with the current time period to determine the cue pattern.

Optionally, the somatosensory stimulation comprises a sequence of vibratory pulses according to the cue pattern.

According to an aspect of the present invention there is provided a computer-implemented method for providing targeted cue delivery to regulate a gait of a user comprising: receiving movement data indicative of a gait of a user from one or more inertial sensors; determining a first cue pattern for a first cue delivery device and a second cue pattern for a second cue delivery device in dependence on the movement data; providing, with a first cue delivery device, somatosensory stimulation to a first leg of the user according to the first cue pattern; and providing, with a second cue delivery device, somatosensory stimulation to a second leg of the user according to the second cue pattern.

BRIEF DESCRIPTION OF THE DRAWINGS

Embodiments of the invention will now be described by way of example only, with reference to the accompanying figures, in which:

FIG. 11A illustrates a 3 m timed up and go (TUG) test path 1110 with a 2.5 m marker. FIG. 11B illustrates a narrowing passage path 1110. Figure 11C shows a four-cornered path 1110, during which the participant was distracted with conversation. FIG. 11D illustrates a complex path 1110 including obstacles. Each path 1110 was walked by each participant under a condition A comprising no intervention, and a condition B comprising intervention with responsive stimulation delivered to determine an effectiveness of a method according to an embodiment of the invention, as described with reference to FIGS. 3 and 7.

FIG. 12A illustrates the average gait freezing duration for eight of the participants of the clinical investigation during the tasks compared between condition A (left) and condition B (right). FIG. 12B illustrates the total time to complete the walking tasks for the eight participants comparing condition A (left) and condition B (right). FIG. 12C illustrates the average stride length for the eight participants during the tasks compared between condition A (left) and condition B (right). FIG. 12D illustrates the average step symmetry for the eight participants during the tasks compared between condition A (left) and condition B (right).

FIG. 13 illustrates a walking map during the walking task under condition A (upper map) compared to a walking map during the walking task under condition B (lower map). It can be seen on the upper map that the participant exhibited severe gait freezing without intervention, which was greatly mitigated by the responsive pulse delivery.

DETAILED DESCRIPTION OF EMBODIMENTS OF THE INVENTION

Figure 1:
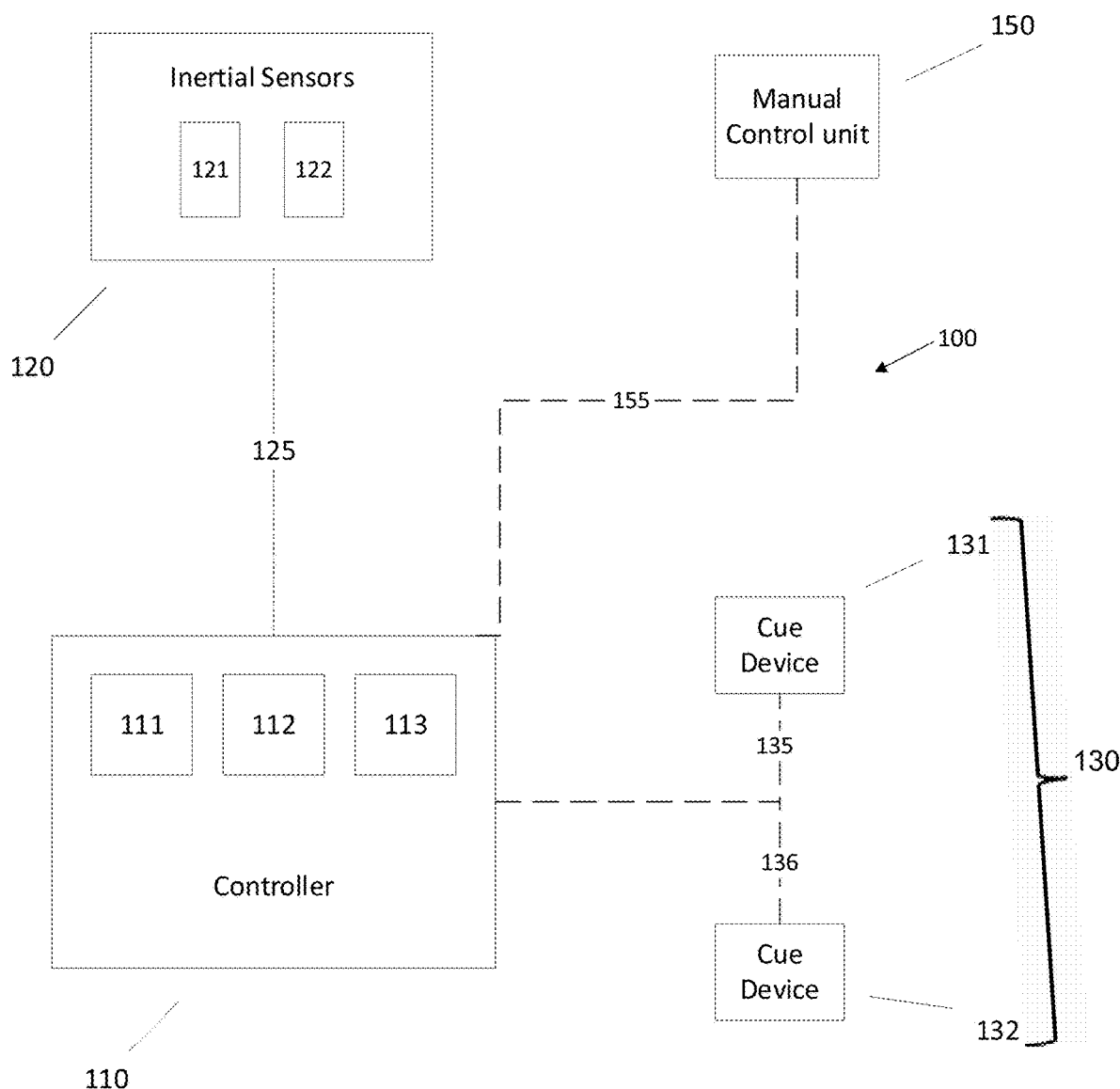
FIG. 1 shows a schematic illustration of a system 100 according to an embodiment of the invention.

FIG. 1 shows a schematic illustration of a system 100 according to an embodiment of the invention. The system 100 may be used to provide targeted cue delivery to regulate a gait of a user, for example responsive to an abnormal gait event, or in anticipation of an abnormal gait event, as will be explained.

The system 100 comprises inertial sensors 120, cue devices 131, 132 and a controller 110. The inertial sensors 120 are configured to output movement data indicative of the gait of a user. The controller 110 is configured to receive the movement data; determine a cue pattern and output a control signal to control the cue delivery devices 131, 132 to provide stimulation to the user according to the cue pattern.

The system 100 illustrated in FIG. 1 comprises two cue delivery devices 131, 132. In other examples the system 100 may comprise one cue delivery device, or more than two cue delivery devices. Each cue delivery device 131, 132 is configured to provide somatosensory stimulation to a user. For example, the somatosensory stimulation may comprise a vibration or other haptic motion. Each cue delivery device 131, 132 may comprise one or more motors configured to deliver the stimulation and means for providing power to the one or more motors, for example a battery. In an illustrated example, the system 100 comprises a first cue delivery device 131 and a second cue delivery device 132, each configured to provide stimulation to a respective leg of the user. Each cue delivery device 131, 132 may be configured to operate according to a determined cue pattern. For example, each cue delivery device 130 may be configured to provide a sequence of vibratory or other haptic pulses to the user according to the determined cue pattern. The cue pattern may be determined by a controller 110 to which each cue delivery device 131, 132 is communicably coupled, as will be explained.

Each cue delivery device 130 may be configured to be worn by a user of the system 100. For example, each cue delivery device 130 may be integrated with a wearable strap or other attachment means suitable for containing the cue delivery device 130 proximal to a leg of the user. An example arrangement of the cue delivery devices 131, 132 will be described with reference to FIG. 2.

The system 100 illustrated in FIG. 1 comprises two inertial sensors 120 responsive to motion of the user. However, in other examples one inertial sensor 120 or more than two inertial sensors 120 may be provided. Each of the inertial sensors 120 may comprise one or more accelerometers and/or gyroscopes and may be configured to collect data indicative of six degrees of freedom (6 DoF) motion. The 6 DoF motion data may be collected by, for example, a 3-axis accelerometer and a 3-axis gyroscope. The inertial sensors may be configured to be worn by a user of the system 100, as will be explained. Each inertial sensor 120 is configured to detect motion of a body part of the user, and to output movement data 125. The inertial sensors 120 may be arranged such that sufficient information may be extracted from the resultant movement data to indicate one or more features of the user's gait. For example, at least one inertial sensor 120 may be arranged to be worn by each leg of the user. Further inertial sensors 120 may be arranged to be worn on other body parts, for example the back or arm of the user to provide more comprehensive movement data 125. However, it will be appreciated that even one inertial sensor 120 may provide sufficient information to extract a number of gait characteristics, for example step frequency (pace) and so according to some examples only one inertial sensor may be provided.

The system 100 illustrated in FIG. 1 comprises a controller 110. In some examples, the functionality of controller 110 may be implemented across a plurality of controllers.

The controller 110 may be operable to control aspects of the system 100 and to optionally record data and communicate with external systems, as will be explained. The controller 110 may comprise at least one memory 112, and at least one processor 111 operable to execute computer readable instructions which may be stored in the memory 112. The controller 110 may perform operations, such as a method according to the invention, on data stored in the memory 112 as will be explained. The controller 110 further comprises a communication module 113 operable to enable communication between the controller 110 and with other elements of the system 100. The communication module 113 may comprise an input/output (I/O) device to enable the communication of data to/from the controller 110 either via circuitry or wireless communication such as Bluetooth, Infrared or Near-Field (NFC) Communication. The communication module 113 may further be communicably coupled to one or more networks 250 such as Local Area Networks (LANs), the Internet and the like. The controller 110 may be controlled in part by software stored on memory 112, executable by processor 111.

The controller 110 is communicably coupled, via the communication module 113, to the inertial sensors 120 and the cue delivery devices 131, 132 via the communication module 113. The controller is operable to receive data from the inertial sensors 120 and store the received data in the memory 112, for processing according to a method of the invention as will be described. The controller 110 is configured to determine a cue pattern for each cue delivery device, as will be explained, and is configured to transmit a control signal 135, 136 to each cue delivery device 131, 132. The control signal 135, 136 may comprise instructions for each cue delivery device 131, 132 to operate according to the determined pulse delivery pattern.

The system 100 may optionally comprise one or more manual control units 150. Reference will be made to one manual control unit 150, however it will be appreciated that more than one manual control unit 150 may be implemented. The manual control unit 150 is configured to receive user input, for example in the form of audio, haptic, or touch input from the user. The manual control unit 150 may comprise one or more input devices such as buttons, key pads or touch screens configured to receive a selection from the user. The manual control unit 150 is communicably coupled to the controller 110 and may be configured to communicate an indication of a user selection or input 155 to the controller 110 via the communication module 113.

Figure 2A:
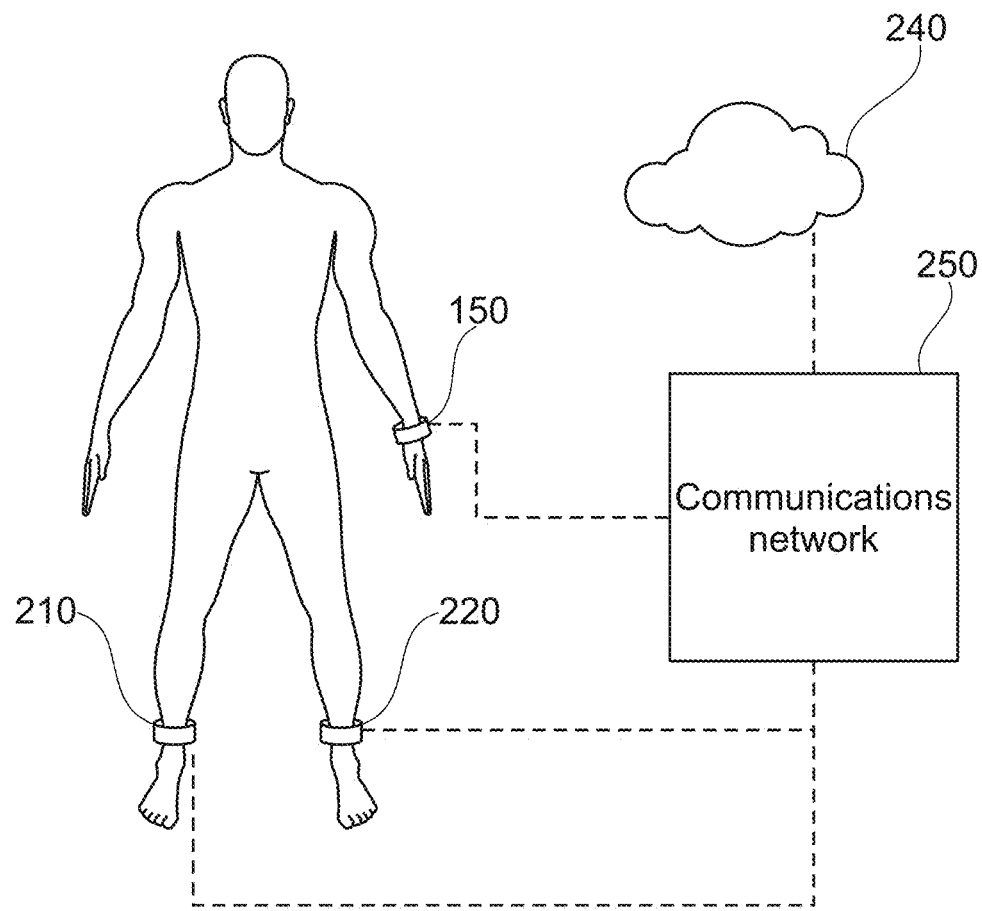
FIGS. 2A and 2B show an example arrangement of the system 100.
Figure 2B:
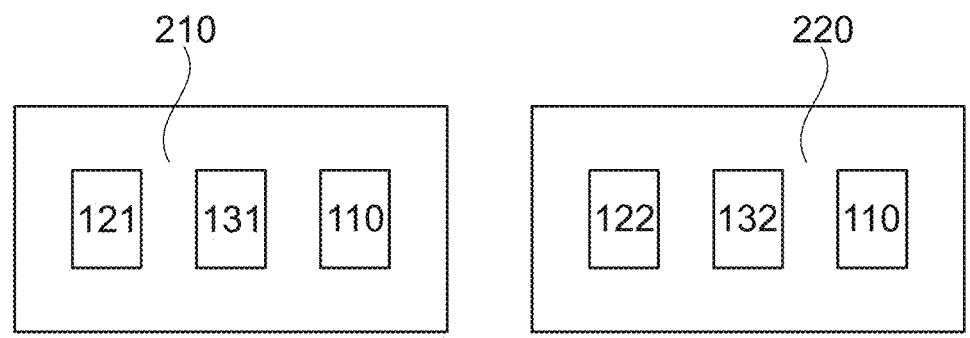

FIGS. 2A and 2B illustrate an example arrangement of the system 100 according to the present invention.

The system 100 may be implemented on a plurality of user devices 210, 220. FIG. 2A illustrates two user devices in an example arrangement in use. It will be appreciated that more or fewer units may be present. Each user device 210, 220 may be arranged to be attachable to a body part of the user. For example, a respective user device 210, 220 may be configured to be attached, in use, to each of a first and second leg of the user as illustrated in FIG. 2A. In some examples, each user device 210, 220 may be arranged to substantially surround an area of the leg, for example in the form of a bracelet device.

Each user device houses at least one of the cue delivery devices 131, 132. In some examples, each user device 210, 220 also houses one or more inertial sensors 120. Alternatively, the inertial sensors 120 may not be housed within the user device 210, 220 but instead may be configured to be placed elsewhere on the body and communicably coupled to each user device 210, 220. Each user device 210, 220 may house a controller 110 as described. In some examples only one user device 210 houses a controller 110, or alternatively the controller 110 may be wholly or in part implemented on an external device communicably coupled to each user device 210, 220.

FIG. 2B illustrates a first user device 210 comprising at least a first inertial sensor 121, a first cue delivery device 131, and a controller 110 comprising a communication module 113; and a second user device 220 comprising at least a second inertial sensor 122, a second cue delivery device 132, and a controller 110 comprising a communication module 113. The first user device 210 may be attachable to a first leg of the user, and the second user device 220 may be attachable to a second leg of the user, as illustrated by FIG. 2A. The controller 110 of the first user device 210 may in some examples be configured to perform at least a substantial part of a method according to the invention, as will be described, and the first user device 210 may be referred to as a primary, or mother user device.

The optional manual control unit 150 may be implemented as a handheld device, a wearable device, a computer, or similar. For example, the optional manual control unit 150 may be implemented on a mobile phone, watch, handheld or wearable remote control, personal computer (PC) or tablet, or any other device capable of receiving input and transmitting data.

The controller 110 may be communicably coupled to one or more cloud based systems 240 via the one or more networks 250. The controller may be configured to transmit data to the cloud based systems 240 for storage, or retrieve data from the cloud based systems 240 for processing according to examples of the invention, as will be explained. Aspects of methods according to the invention may also be implemented wholly or in part by processing means on the cloud based systems 240.

Figure 3:
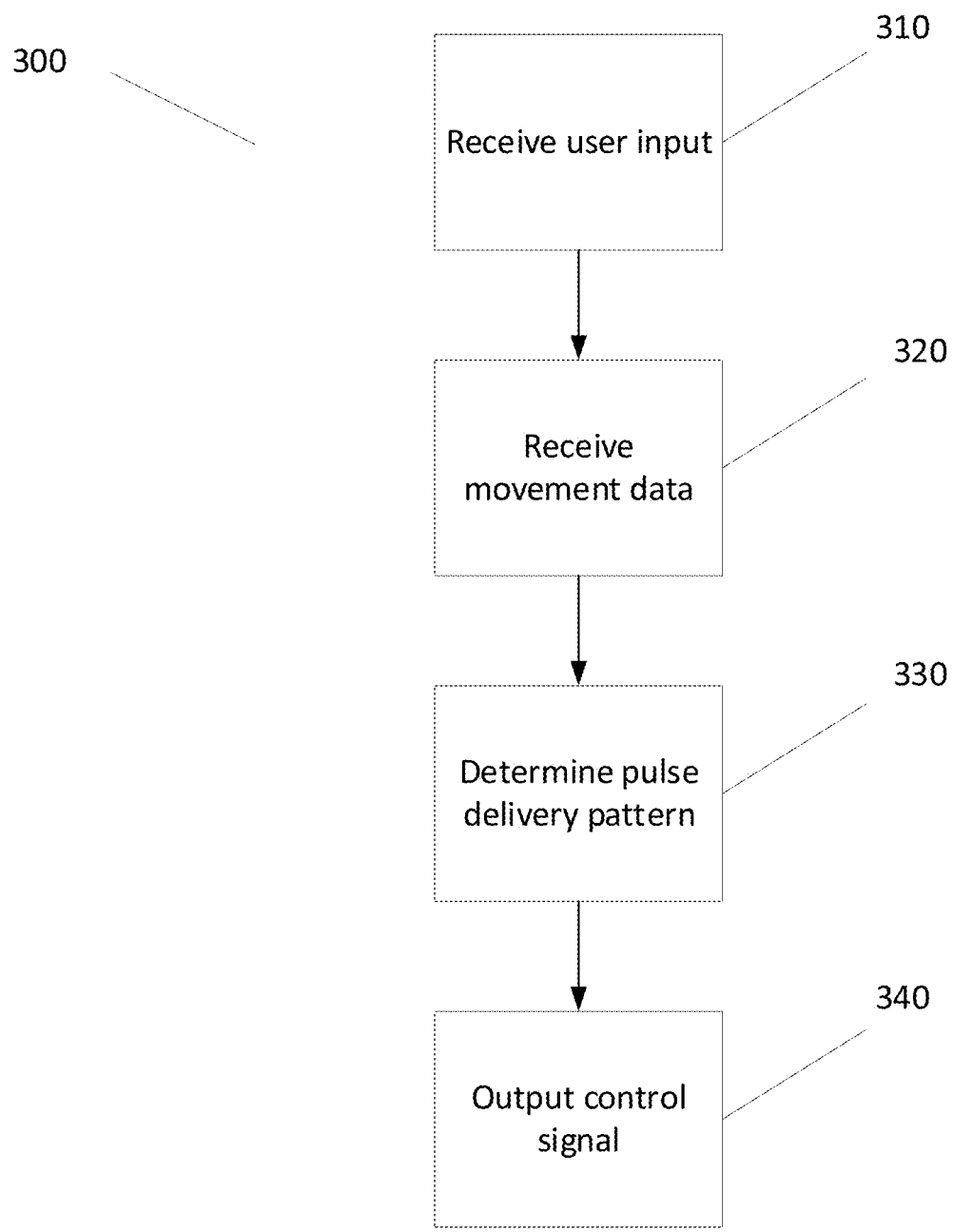
FIG. 3 shows a method 300 according to an embodiment of the invention.

FIG. 3 shows a method 300 according to an example of the invention. The method 300 may be implemented by the system 100, in particular controller 110, described above such as by computer-readable instructions being executed by the processor 111.

The method 300 optionally comprises a step 310 of receiving user input. The user input may be received by the manual control unit 150. Information indicative of the user input may be communicated from the manual control unit 150 to the controller 110, for example the controller 110 implemented in the primary feedback device 210. The user input may comprise an indication of a desired mode of operation for the system 100. The controller 110 may be configured to receive the indication of a desired mode of operation, and implement a method corresponding to the desired mode of operation. Example modes of operation may comprise a rhythmic mode, a responsive mode, and a manual mode, as will be explained.

In some examples, the mode of operation may be predetermined and thus the method 300 may not comprise step 310.

The method 300 comprises a step 320 of receiving movement data 125. The movement data 125 may be received by the controller 110, for example implemented on the primary user device 210 or on an external device, as has been explained. The movement data 125 is received from the one or more inertial sensors 120 via the communication module 113. In one example, first movement data is received from the first inertial sensor 121 indicative of inertial motion of the first leg, and second movement data is received from the second inertial sensor 122 indicative of inertial motion of the second leg. The first movement data and second movement data may be indicative of 6 DoF inertial motion of each leg.

The movement data 125 may be received by the controller 110 substantially in real time, as the user moves. Step 320 may comprise storing an indication of the movement data 125 in memory 112 as the movement data is received, for subsequent processing. Step 320 may further comprise communicating the movement data 125 to the one or more cloud-based systems 240.

The method 300 comprises a step 330 of determining a cue pattern for each of the first and second cue delivery devices. The cue pattern is determined in dependence on the movement data 125, and optionally further in dependence on the user selection or input 155. The cue pattern may be determined differently in dependence on the mode of operation of the system 100, as will be explained with reference to FIGS. 5 to 8. The cue pattern may be selectively determined in dependence on a quality of the gait of the user, for example only when it is determined the gait of the user is abnormal. This will be described in more detail with reference to FIGS. 5 and 7.

Figure 4:
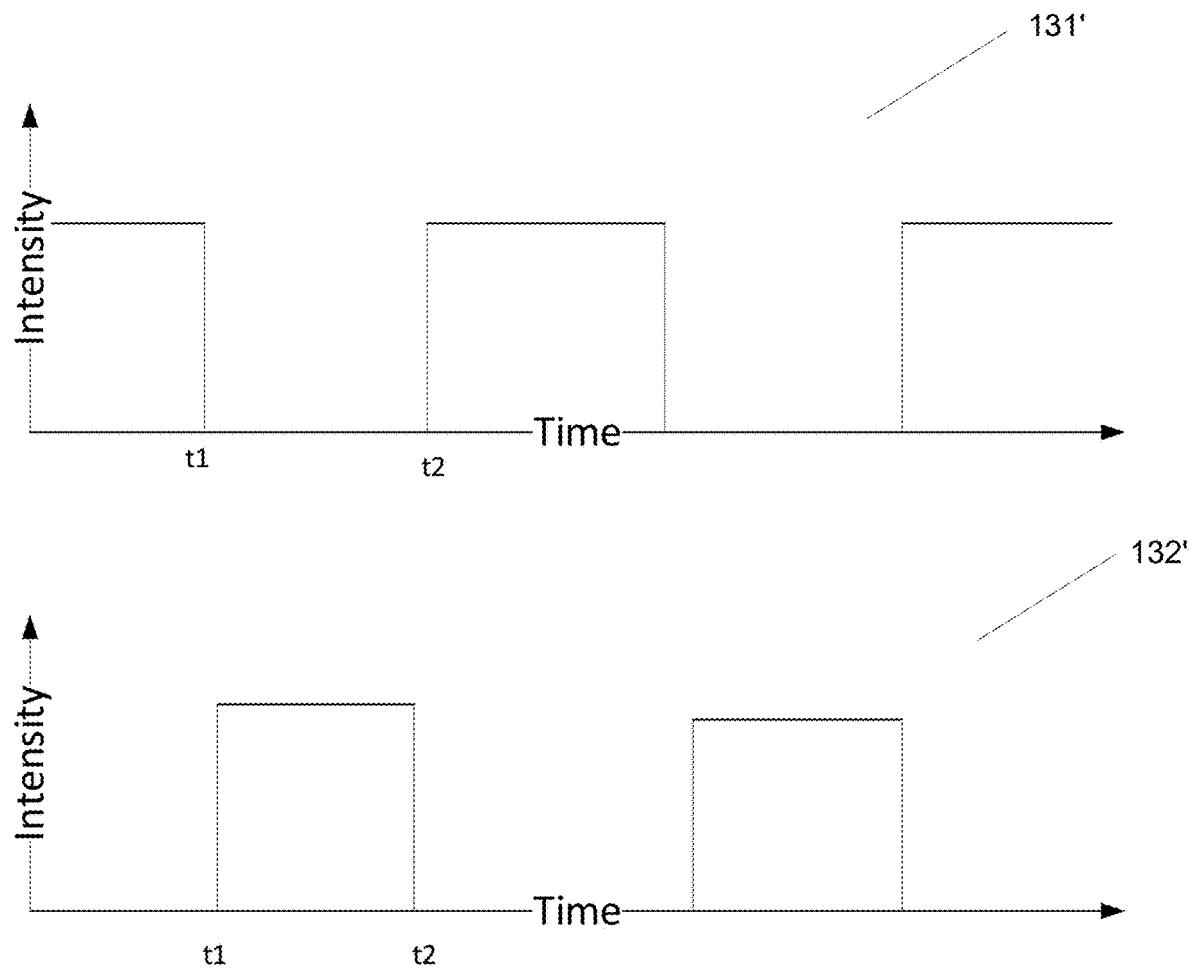
FIG. 4 shows an example cue pattern according to an embodiment of the invention.

The cue pattern may indicate the intensity of stimulation provided by each cue delivery device as a function of time. An example cue pattern 131', 132' is illustrated in FIG. 4, for two cue delivery devices 131, 132. The example cue pattern illustrated comprises a sequence of alternating pulses across the two devices, however a variety of alternative cue patterns may be utilised, as will be explained.

The method 300 comprises a step 340 of outputting a control signal 135, 136 to each cue delivery device 131, 132. The control signal 135, 136 is communicated to control the cue delivery devices to provide stimulation to the user according to the cue pattern. For example, each control signal 135, 136 may act to control the intensity at which the motor of each cue delivery device operates, and the temporal sequence of operation. For example, given the determined cue pattern illustrated in FIG. 4, the control signal 135, 136 may act to control the cue delivery devices 131, 132 to provide alternate pulses of stimulation at a given intensity.

According to some examples of the present invention, the system 100 may be configured to operate in a rhythmic mode. In the rhythmic mode, the system 100 is configured to provide stimulation to the user at a steady rhythm to aid the user in regulating features of their gait such as step frequency or stride length. By regulating step frequency when certain gait features surpass a threshold, more dangerous gait events such as Freezing of Gait (FoG) may be avoided or reduced in number.

Optionally, the configuration of the system 100 may be determined by the user input received in step 310. The user input may indicate a selected mode of operation, as has been explained, which may comprise a selection of a rhythmic mode. Alternatively, the system 100 may be configured to automatically operate at least in part in the rhythmic mode, and to perform the method illustrated in FIG. 5 during step 330.

Figure 5:
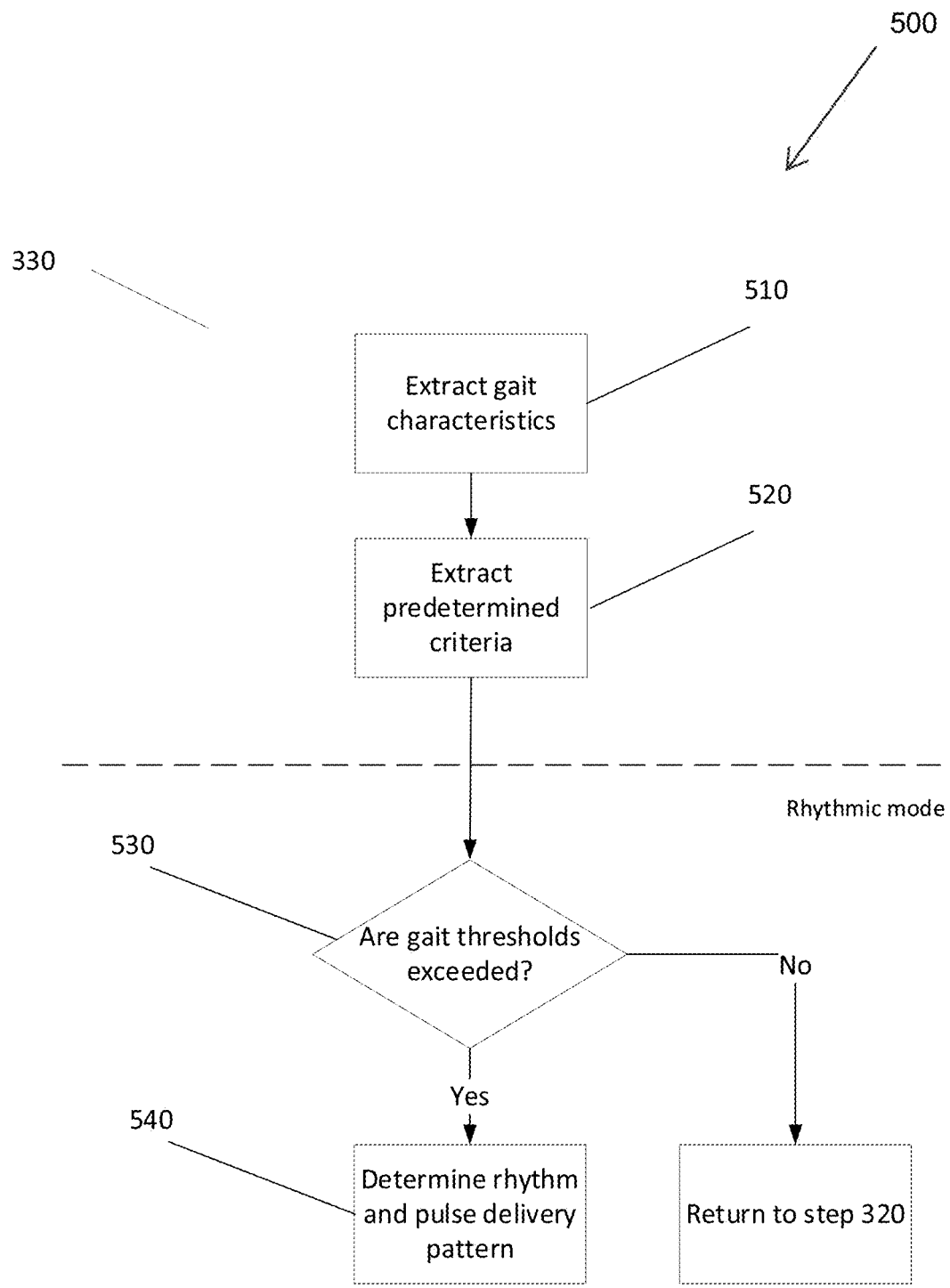
FIG. 5 shows a rhythmic method according to an embodiment of the invention.

FIG. 5 illustrates an example a rhythmic method 500 of determining a rhythmic cue pattern during operation of the method 300. The rhythmic method 500 may be performed as part of step 330.

The rhythmic method 500 may comprise a step 510 of extracting gait characteristics from the movement data 125.

Step 510 may comprise pre-processing the movement data. The pre-processing may comprise cleaning the movement data 125 by removing irrelevant and erroneous values. The pre-processing may comprise removing segments, i.e.

windows of time, of the movement data 125 where the user is not walking. Non-walking segments of the movement data 125 may be identified by applying a windowed Fourier transform to one or more axes of the movement data, for example to one axis of the movement data extracted from a 3-axis accelerometer. Segments of the movement data 125 with energy below a predetermined threshold on high frequency components may then be identified as non-walking segments, for example on frequency components above 0.5 Hz. Similarly, segments of the movement data 125 with erroneously high energy in these high frequency components may indicate corrupted data, and the pre-processing may comprise removing these corrupted segments.

Step 510 then comprises extracting one or more gait characteristics from the movement data 125. The gait characteristics may comprise any parameter of the movement data 125 that may provide an indication of the user's gait. Step 510 may comprise extracting the gait characteristics for each window of the movement data 125, wherein a window of the movement data 125 may define a time period, for example 1 second or 1 minute.

In some examples the gait characteristics may comprise an indication of pace of the user, for example a step frequency of the user. The step frequency may be extracted from the movement data by identifying steps taken in one or more axes. Accurate step frequency may be extracted from the Z-axis of the 3-axis accelerometer and/or gyroscope data, utilising a peak detection algorithm. The step frequency may then be estimated in dependence on the number of steps performed in the window.

The gait characteristics may comprise an indication of the user's stride, for example a stride length of the user. The stride length may be estimated by extracting from the movement data 125 an average distance travelled by the user with each step taken. The gait characteristics may comprise an indication of the user's step symmetry, in dependence on a difference between the movement data 125 relating to the first leg and the movement data 125 relating to the second leg.

The rhythmic method 500 may comprise a step 520 of extracting predetermined criteria. The predetermined criteria may be stored in memory 112, or on the one or more cloud-based systems 240 and may be retrieved by the controller 110. In some examples, sub-step 520 may comprise determining the criteria by the controller 110 in real time.

In the rhythmic mode, the predetermined criteria comprise one or more thresholds for gait characteristics extracted in sub-step 520. For example, the predetermined criteria may comprise a minimum or maximum threshold for one or more of the extracted gait characteristics, such as a minimum or maximum pace threshold, stride length threshold, or step symmetry threshold.

As mentioned, in some examples, the criteria may be determined in step 520 by the controller 110. The controller 110 may be configured to determine the criteria in dependence on historic movement data associated with the user. If movement data 125 associated with the user has been stored, for example in memory 112 or on one or more cloud-based systems 240, step 250 may comprise extracting a portion of historic movement data 125. The portion extracted may be flagged or marked as being indicative of normal gait. Step 520 may then comprise determining one or more thresholds for gait characteristics in dependence on the gait characteristics during the historic movement data 125.

An average value of the gait characteristic may be determined over the historic movement data 125, and the thresholds may be determined to be a deviation from the average value, for example a relative deviation of 10% or 20% or a predetermined absolute deviation.

In one example according to the rhythmic mode, the extracted gait characteristics comprise a pace of the user. The predetermined criteria may then comprise a pace threshold. The pace threshold may comprise a relative deviation from the historic average pace of the user, for example 10% although any reasonable value may be chosen. The predetermined criteria may comprise a maximum pace threshold, i.e. specifically a relative deviation above the average pace of the user. Defining only a maximum pace threshold may be beneficial as a quickening of step frequency may pose more of an increased risk to the user than a slowing of step frequency, particularly of festination or FoG events.

Optionally, step 520 may comprise receiving an indication of a fall risk for the user, for example as 'high' fall risk or 'low' fall risk. The indication may comprise a fall frequency, for example an average number of falls for a given time period such as a week. The fall risk may have been pre-selected by the user of the system 100 during an initial setup of the system, and may be stored in the memory 112 or otherwise accessible by the controller 110. Step 520 may comprise determining the criteria further in dependence on the fall risk for the user. Step 520 may comprise determining the criteria more conservatively for users having a high fall risk. For example, if the criteria comprise a pace threshold, the pace threshold may be determined as a 20% deviation for users with a 'low' fall risk but a lower deviation, e.g. 10%, for users with a 'high' fall risk.

The method 500 may comprise a step 530 of determining whether the extracted gait characteristics meet the predetermined criteria. For example, if the extracted gait characteristics comprise a pace of the user and the predetermined criteria comprise a maximum pace threshold, step 530 comprises determining whether the pace of the user exceeds the pace threshold.

If the extracted gait characteristics do not meet the predetermined criteria, no cue pattern is determined and no stimulation is provided by the cue delivery devices. The movement data is continued to be monitored according to step 320 and 510 to 530.

If the extracted gait characteristics meet the predetermined criteria, it is determined that the user's gait is abnormal and a cue should be provided to the user to regulate their gait. The rhythmic method 500 may then proceed to step 540.

Step 540 comprises determining a rhythm and a cue pattern for the user to aid gait regulation. According to the rhythmic mode of operation, the cue pattern may be determined to be intermittent stimulation by at least one cue delivery device at a rhythm corresponding to an appropriate pace for the user. The appropriate pace may be predetermined and retrieved from memory 112. In some examples, the controller 110 is configured to determine the appropriate pace in dependence on historic movement data associated with the user, analogously to the determination of the pace threshold. The appropriate pace for the user may be determined as the user's historic average pace. In some examples, the appropriate pace for the user may be determined in real time as an incremental change to their current pace, in order to aid them to slowly return below the pace threshold. For example, the appropriate pace may be constantly determined in real time as 10% slower than the user's current walking pace, or any other reasonable proportion. In this way if the user is significantly above the pace threshold they will be encouraged to gradually slow down in a natural and minimally perceptible way.

Optionally, an intensity of the stimulation may be determined in dependence on a level of abnormality of each of the gait characteristics. For example, the further in excess of the threshold the extracted characteristic lies, the more intense the stimulation may be determined to be. The stimulation may then be gradually reduced to zero the closer the extracted characteristic lies to the threshold.

The rhythmic method 500 may comprise continuing to monitor the extracted gait characteristics while stimulation is being provided, and to cease providing stimulation or reduce the intensity of the stimulation if a second set of predetermined criteria are met. The second set of predetermined criteria may comprise the same thresholds as the first set. For example, if the first predetermined criteria comprise the pace of the user exceeding 10% higher than an average pace, the second set of predetermined criteria may comprise the pace of the user dropping back below this threshold. However, in some examples the second set of predetermined criteria may be different. For example, the second set of predetermined criteria may comprise a closer threshold to the average pace (or other characteristic) of the user, to ensure that normal gait is restored before ceasing stimulation.

Figure 6:
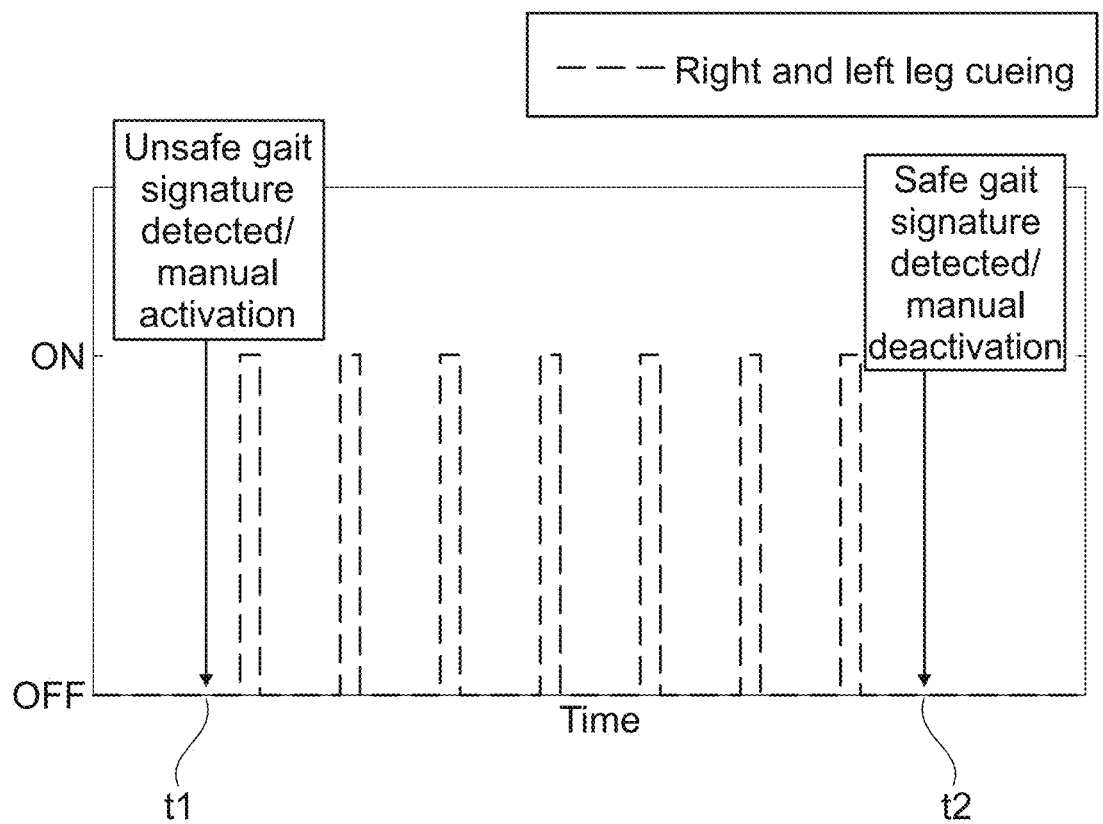
FIG. 6 illustrates an example rhythmic cue pattern according to an embodiment of the invention.

An example rhythmic cue pattern determined during step 540 is illustrated in FIG. 6.

At time t1, it is determined that one or more determined thresholds have been exceeded, e.g. a pace threshold. The controller determines a cue pattern and outputs a control signal to at least one cue delivery device. FIG. 6 illustrates an example cue pattern applied to two cue delivery devices. The cue pattern comprises a sequence of pulses presented at a determined rhythm, which may be an appropriate pace for the user, as has been discussed. At time t2, stimulation is ceased. This may be because the controller 110 has determined that a second set of predetermined criteria have been satisfied, i.e. the user has returned to a normal gait, or stimulation may be manually deactivated by the user via the manual control unit 150.

The cue pattern of FIG. 6 illustrates a single intensity of stimulation. However as has been discussed, this may vary depending on the level of abnormality of the gait characteristics, and may change over time while the stimulation is being provided. The interval between the pulses and the duration of each pulse may also vary in dependence on the level of abnormality In some examples of method 300, the system 100 may be configured to operate in a responsive mode. In the responsive mode, the system 100 is configured to detect a Freezing of Gait (FoG) event or a festination event. One example will be described with reference to FoG detection, however it will be appreciated that the method is also applicable to festination detection with appropriate alteration of the gait characteristics used for identification of the event. When an FoG event is detected the system is configured to provide stimulation to a first leg of the user until a step is taken, then switch to deliver the cue to the other leg. This alternating pattern may be maintained until the user re-establishes normal gait. By prompting the user in co-ordination with the current gait cycle, normal gait may be re-established more quickly.

Figure 7:
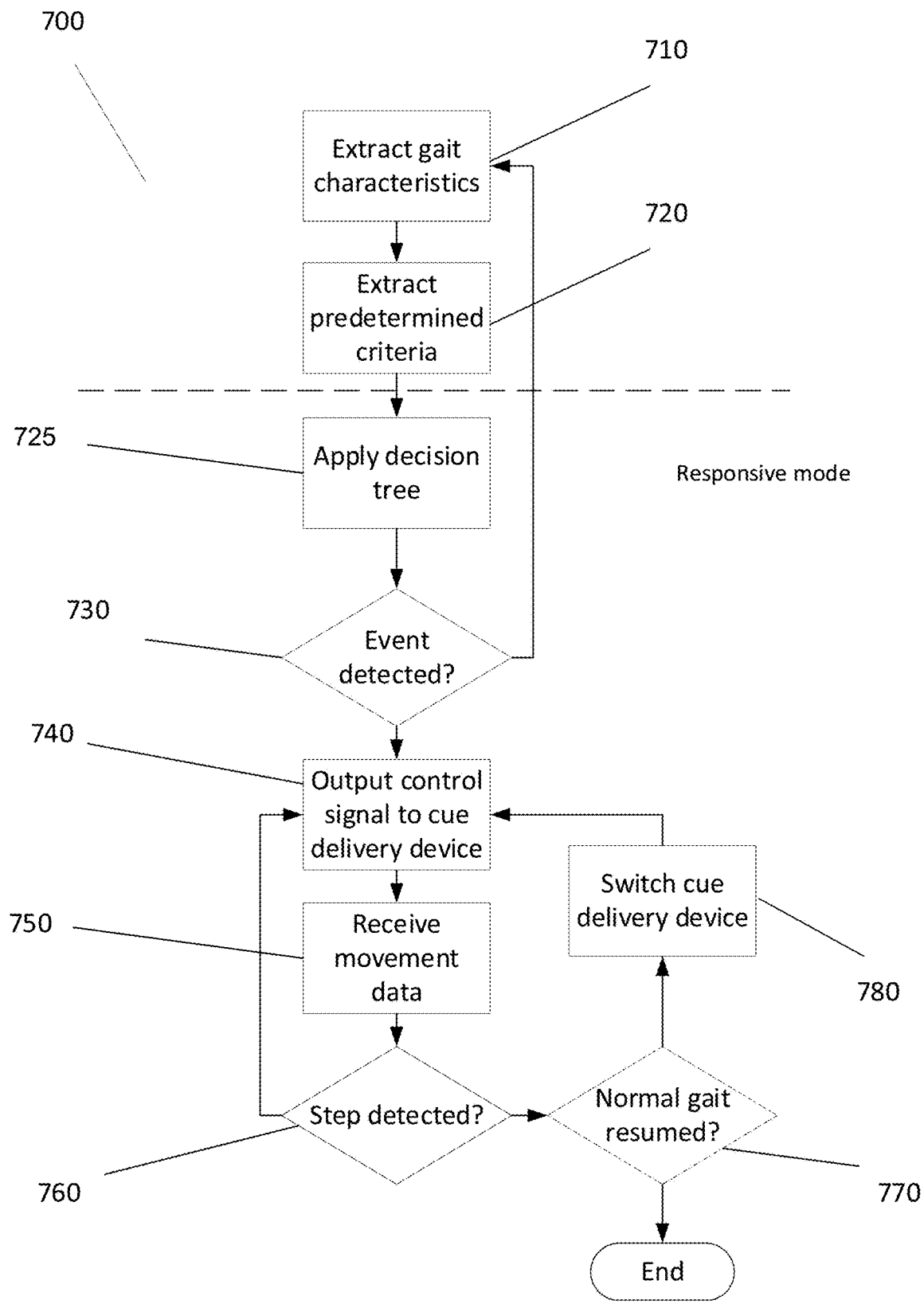
FIG. 7 shows a responsive method according to an embodiment of the invention.

FIG. 7 illustrates an example responsive method 700 of identifying FoG or festination events and determining a responsive cue pattern during operation of the method 300.

The responsive method 700 may be performed as part of step 330 and step 340. Method 700 may in some examples be performed in conjunction with the rhythmic method 500. For example, the rhythmic method 500 may be utilised initially to prevent abnormal gait events occurring when characteristics of the user's gait exceed a threshold, as has been explained. The method 700 may be concurrently implemented to detect any abnormal gait events such as FoG. If an abnormal gait event such as FoG is detected, a responsive cue pattern may be implemented according to the method 700. The user may select, for example via the manual control unit 150, whether the system should operate in responsive mode, rhythmic mode, or a combination of the two.

The responsive method 700 may comprise a step 710 of extracting gait characteristics from the movement data 125.

Step 710 may be performed analogously to step 510. One or more of the extracted gait characteristics of the movement data 125 may be specifically associated with an FoG or festination event, and thus may be particularly useful for event detection with relation to the responsive method 700.

The movement data 125 may be indicative of a plurality of frequency bands each corresponding to a range of frequency of movement. For example, the movement data 125 may comprise 6 DoF inertial motion data from a 3-axis accelerometer and a 3-axis gyroscope as has been explained. Applying a Fourier transform to each axis of the movement data yields a frequency distribution of the motion which may be divided into the plurality of frequency bands. One or more gait characteristics may be extracted in dependence on the power spectral density of one or more frequency bands. In some examples the gait characteristics comprise one or more of a power of a first frequency band associated with walking, a power of a second frequency band associated with freezing of gait, and a ratio of the power of the first and second frequency bands (hereinafter referred to as a 'freeze index').

The gait characteristics may comprise one or more parameters indicative of an entropy of the movement data 125.

Gait characteristics may be extracted from the movement data 125 by applying one or more wavelet transforms to the movement data 125. An example of applying a wavelet transform to the movement data 125 is illustrated in FIG. 10.

Figure 10:
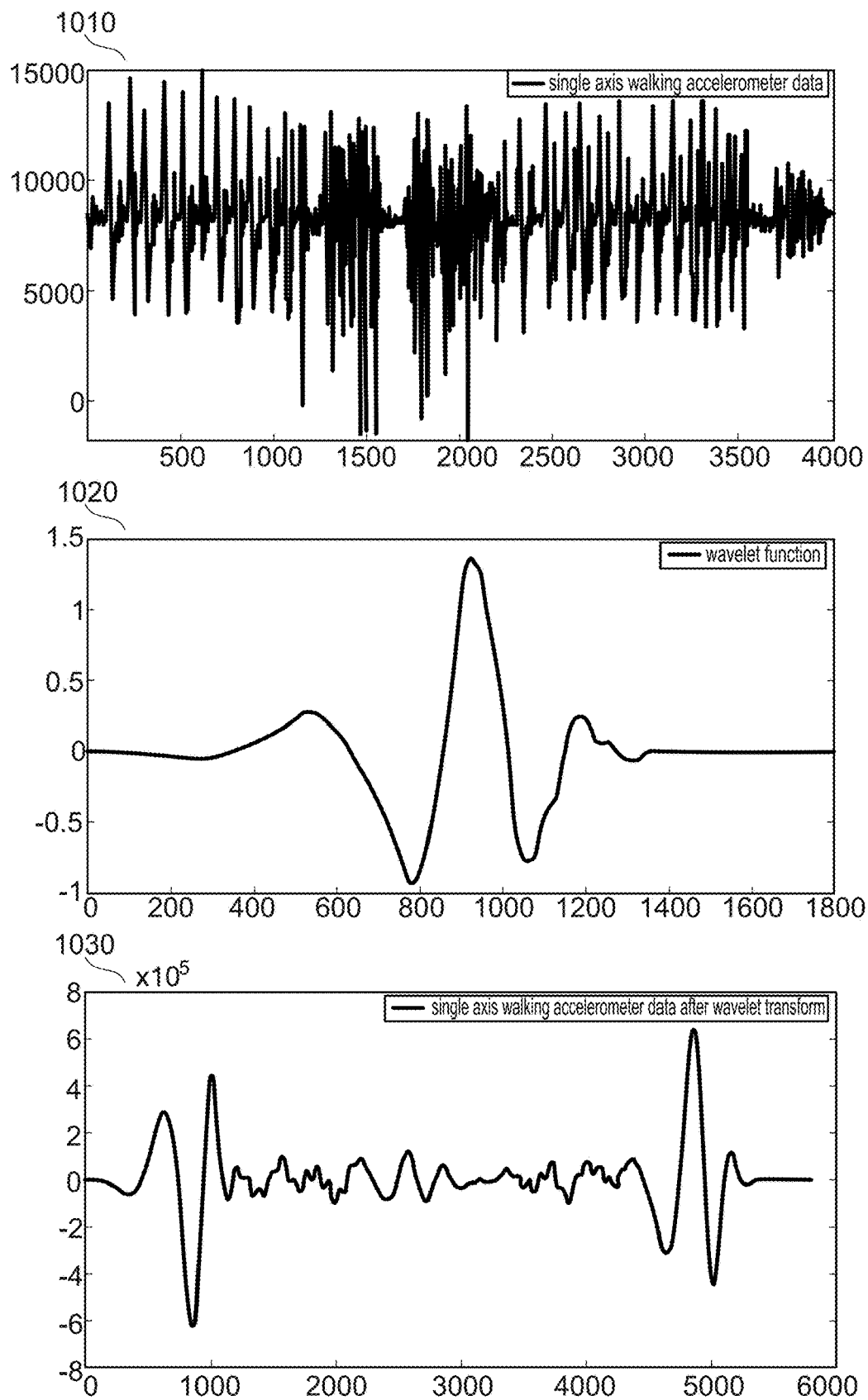
FIG. 10 illustrates an example wavelet transform.

FIG. 10 illustrates an example raw 1 axis accelerometer data 1010 which may be extracted from the movement data 125, and an example wavelet function 1020. A new signal 1030 may be obtained by applying the wavelet function 1020 to the accelerometer data 1010. One or more gait characteristics may then be extracted from the new signal 1030. The wavelet function 1020 may be selected or modified to highlight the weights of one or more predetermined frequency bands of the accelerometer data 1010.

The wavelet function 1020 may be applied to data extracted from one or more time windows of the movement data 125, in order to highlight predetermined characteristics of the movement data 125 over time.

The responsive method 700 may comprise a step 720 of extracting predetermined criteria. The step 720 may be performed analogously to step 520 as described. The predetermined criteria may be stored in memory 112, or on the one or more cloud-based systems 240 and may be retrieved by the controller 110. In some examples, step 720 may comprise determining the criteria by the controller 110 in real time.

In the responsive mode, the predetermined criteria may comprise a threshold of likelihood of an FoG or festination event. For example, the threshold may be a likelihood of 50% or 80% that an FoG event has occurred, although it will be appreciated that any likelihood may be used. The likelihood may be associated with a decision tree or other machine learning algorithm to be applied to the movement data 125, as will be explained. In some examples, the likelihood threshold may comprise the classification of the gait characteristics as indicative of an FoG event by the decision tree, as will be explained.

The responsive method 700 comprises a step 725 of applying a decision tree or other trained machine learning algorithm to the extracted gait characteristics. For example, the decision tree may be a random forest classifier, a support vector machine (SVM) or a neural network. In practice, the decision tree may be a plurality of decision trees. The decision tree or other algorithm may be trained to classify a set of gait characteristics as indicative of normal gait, a FoG event or a festination event. The decision tree or other algorithm may further associate a likelihood or other level of certainty with the classification.

In some examples of the invention, the method 300 or 700 may comprise training the decision tree. The decision tree may be trained by the controller 110 or on the cloud-based systems 240. The decision tree may be trained using sample gait characteristics indicative of normal gait and FoG events. The sample gait characteristics may comprise training data annotated as 'normal', 'FoG' or 'festination'. Further annotations may also be used, such as 'not walking' for example. According to some examples, at least some of the sample gait characteristics used to train the decision tree may be extracted from historic movement data associated with the user, thereby providing a personalised classification trained on the individual's walking style.

The method 700 comprises a step 730 of determining whether an abnormal gait event, for example an FoG event, has been detected. The determination may be made in dependence on whether the classification outcome of the decision tree meets the extracted predetermined criteria. For example, step 730 may comprise determining whether the gait characteristics have been classified as an FoG event by the decision tree. Step 730 may further comprise determining whether the classification meets a particular likelihood threshold or confidence level, for example whether the gait characteristics have been classified as an FoG event with a determined level of certainty.

If it is determined that an abnormal gait event has been detected, the method 700 proceeds to step 740. Step 740 comprises determining a cue pattern and outputting a control signal to a cue delivery device corresponding to the cue pattern.

In the responsive mode, the cue pattern is determined to comprise a unilateral cue for the first leg by the first cue delivery device 131. The unilateral cue may comprise a sequence of intermittent pulses, continuous stimulation, or any alternative pattern provided only to the first leg. A control signal is communicated to the first cue delivery device 131 to provide the unilateral cue to the first leg.

During provision of the unilateral cue by the first cue delivery device, method 700 comprises a step 750 of continuing to receive movement data 125 indicative of the user's gait.

The method 700 comprises a step 760 of determining whether a step has been taken by the first leg responsive to the cue. A step may be detected for example by identifying a peak in the motion within the accelerometer and gyroscope data, as has been discussed. If no step is detected, it is determined that the first leg is still in a frozen state, and the controller 110 is configured to control the first cue delivery device to continue providing the unilateral cue.

If a step is detected, the method may proceed to step 780. In step 780, responsive to the step being taken by the first leg, the controller may output a control signal to swap the unilateral stimulation from the first cue delivery device to the second cue delivery device. Therefore, once the user has taken a step with the first leg, the stimulation swaps to the second leg to prompt the user to take a next step.

The method 700 may continue operating in this cycle, switching the side of the unilateral cue in dependence on where the user is in the gait cycle.

The method 700 may optionally comprise a step 770 of identifying whether a normal walking pattern has been resumed by the user. For example, step 770 may comprise identifying whether one or more gait characteristics have returned to normal thresholds, analogously to the description surrounding ceasing the rhythmic cue. If a normal walking pattern has been resumed, the method 700 may be configured to terminate cue delivery. The controller 110 may output a control signal to each cue delivery device in operation to cease providing stimulation to the user.

Figure 8:
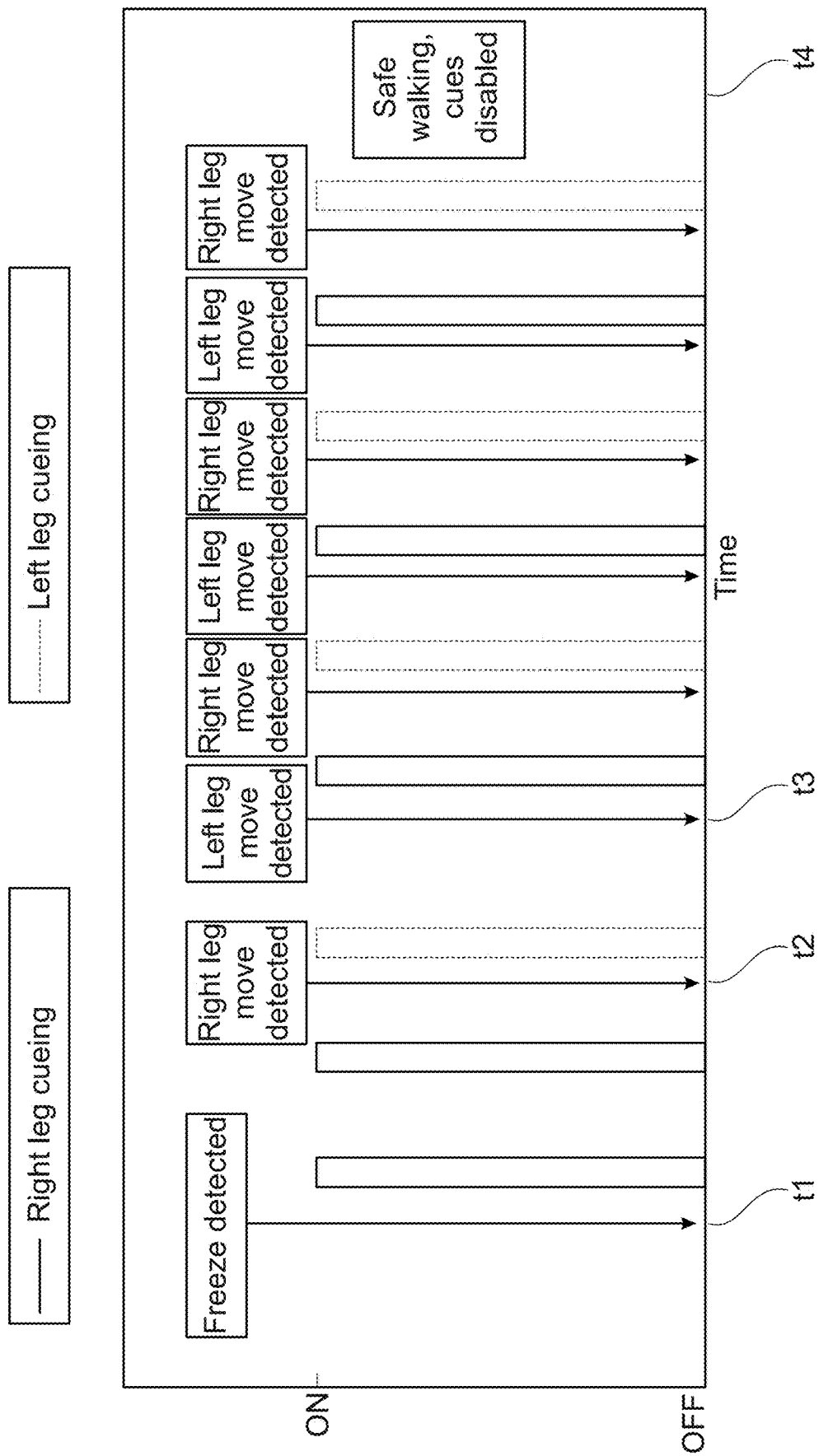
FIG. 8 illustrates an example responsive cue pattern according to an embodiment of the invention.

An example responsive cue pattern determined and implemented during method 700 is illustrated in FIG. 8.

At time t1, it is determined that a FoG event has occurred, for example by classification of gait characteristics as 'FoG' by a random forest classifier or other method as discussed. The controller outputs a control signal to at least one cue delivery device arranged on the first leg of the user. The cue pattern comprises a unilateral cue for the first leg. In this example, a first cue delivery device is configured to provide a sequence of pulses to the first leg while the first leg is in a frozen state. The sequence of pulses may in some examples be an appropriate pace for the user, analogous to the rhythmic cue. At time t2, a step taken by the first leg is detected. Responsive to the step being taken, the unilateral cue is switched from the first delivery device to the second delivery device. The second delivery device provides the unilateral cue to the second leg, and the first delivery device ceases stimulation. At time t3, a step taken by the second leg is detected, and responsive to the step the unilateral cue is switched back to the first delivery device. This pulse delivery sequence is maintained in co-ordination with the gait cycle of the user until a time t4 when it is determined that a normal gait has been resumed by the user, and all stimulation is ceased by the first and second cue delivery devices. Alternatively, stimulation may be manually deactivated by the user via the manual control unit 150.

The cue pattern of FIG. 8 illustrates a single intensity of stimulation. However according to some examples, the intensity may be reduced as the user approaches normal gait characteristics.

Example results obtained from implementing an embodiment of the system 100 and the method 300 with a responsive pulse delivery pattern of method 700 will be described with reference to FIGS. 11A to 13.

Figure 11A:
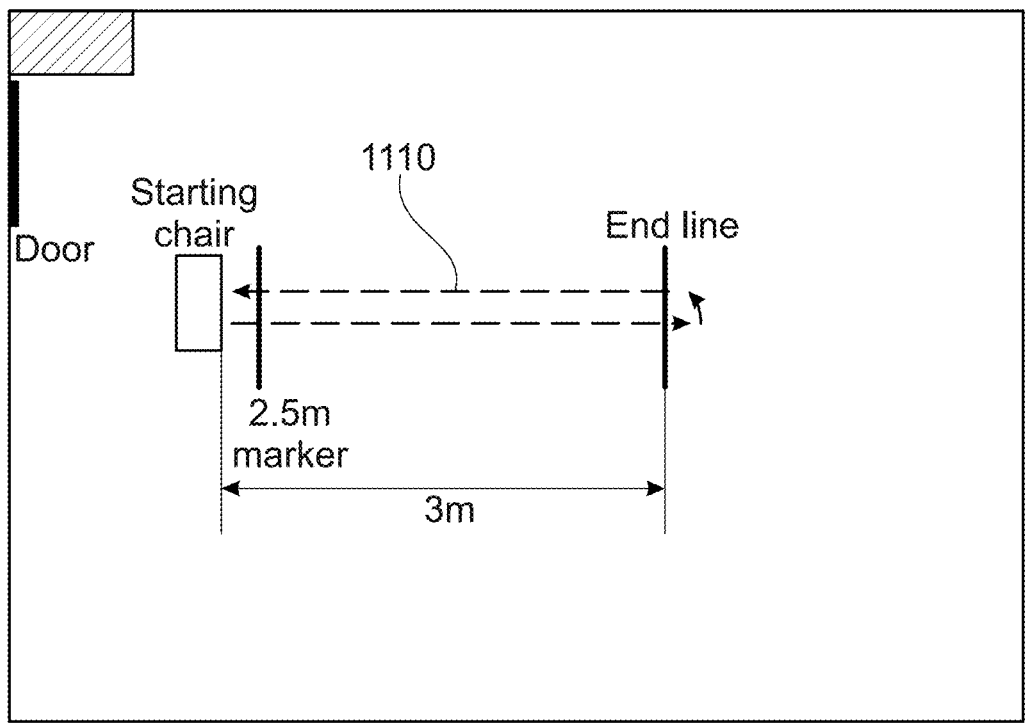
FIG. 11A-11D: Walking Task Illustrations. A clinical investigation was performed using participants with Parkinson's Disease. Each participant performed a series of walking tasks designed to induce Freezing of Gait (FoG) events, with and without intervention provided by a system 100 according to an embodiment of the invention. The walking tasks are illustrated in FIGS. 11A to 11D, with the path walked by the participant marked as path 1110 in each FIGURE.
Figure 11B:
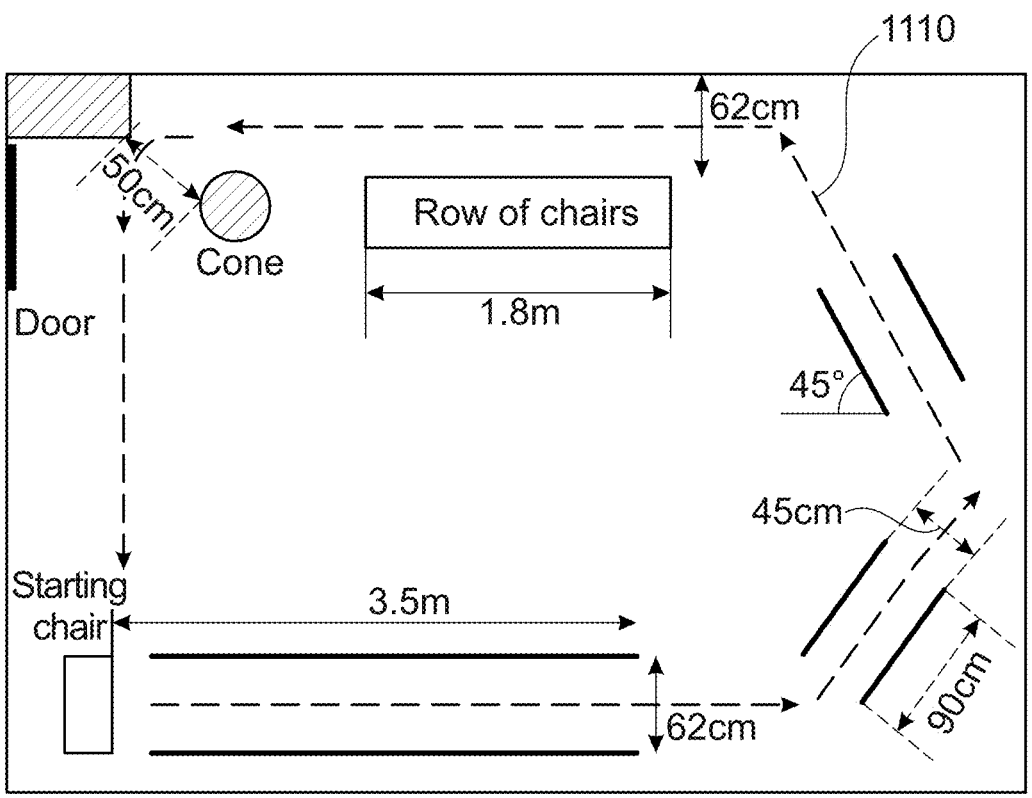
Figure 11C:
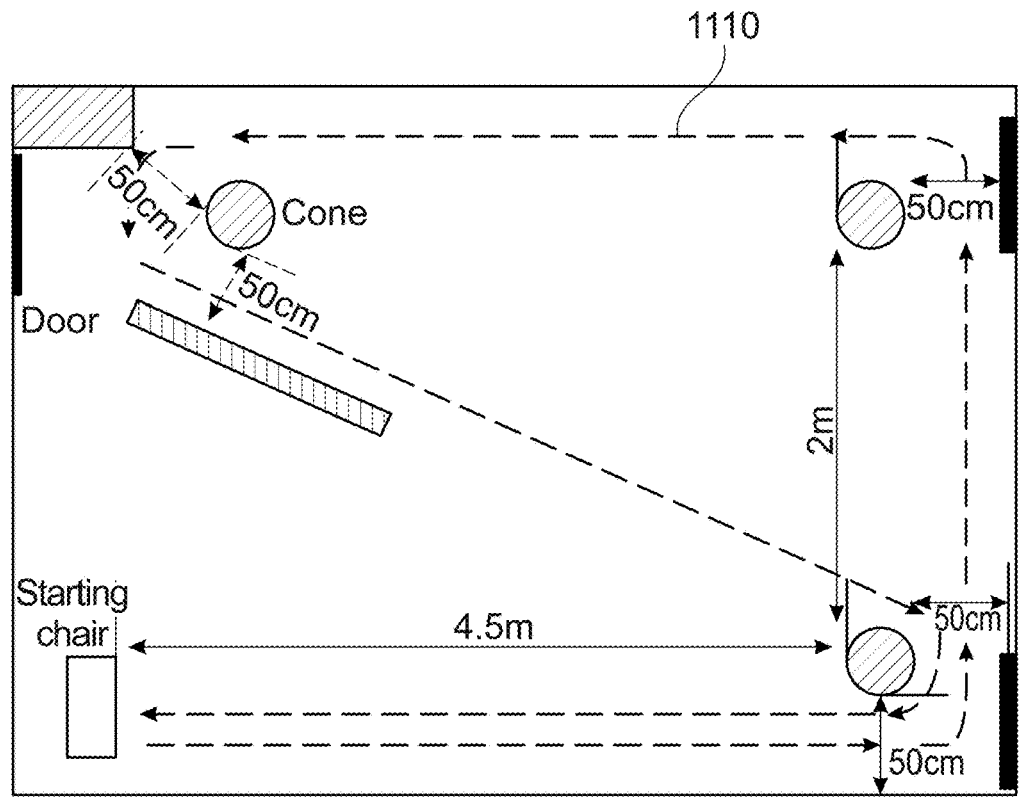
Figure 11D:
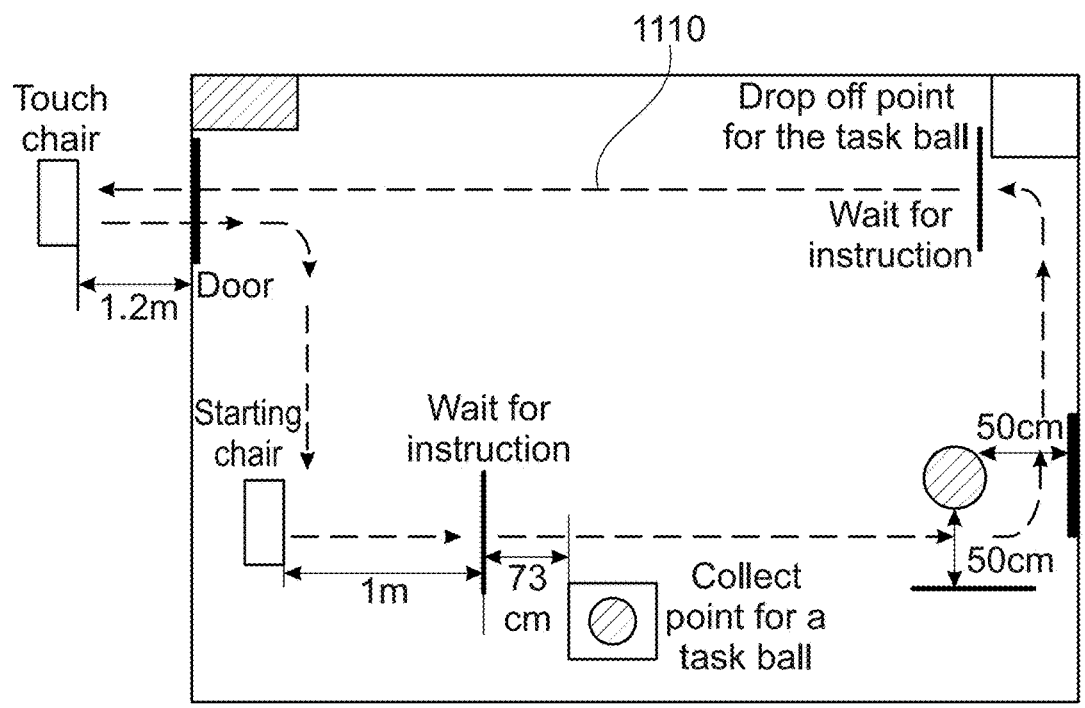

A clinical investigation was performed using participants with Parkinson's Disease. Each participant performed a series of walking tasks designed to induce Freezing of Gait (FoG) events, with and without intervention provided by a system 100 according to an embodiment of the invention. The walking tasks are illustrated in FIGS. 11A to 11D, with the path walked by the participant marked as path 1110 in each Figure. FIG. 11A illustrates a 3 m timed up and go (TUG) test path 1110 with a 2.5 m marker. FIG. 11B illustrates a narrowing passage path 1110. FIG. 11C shows a four-cornered path 1110, during which the participant was distracted with conversation. FIG. 11D illustrates a complex path 1110 including obstacles. Each path 1110 was walked by each participant under a condition A comprising no intervention, and a condition B comprising intervention with responsive stimulation delivered to determine an effectiveness of a method according to an embodiment of the invention, as described with reference to FIGS. 3 and 7.

Stepping of the participant and gait freezing (FoG) events were labelled by blinded observers to extract quantitative gait features. The group results for the eight participants are illustrated in FIGS. 12A to 12D.

Figure 12A:
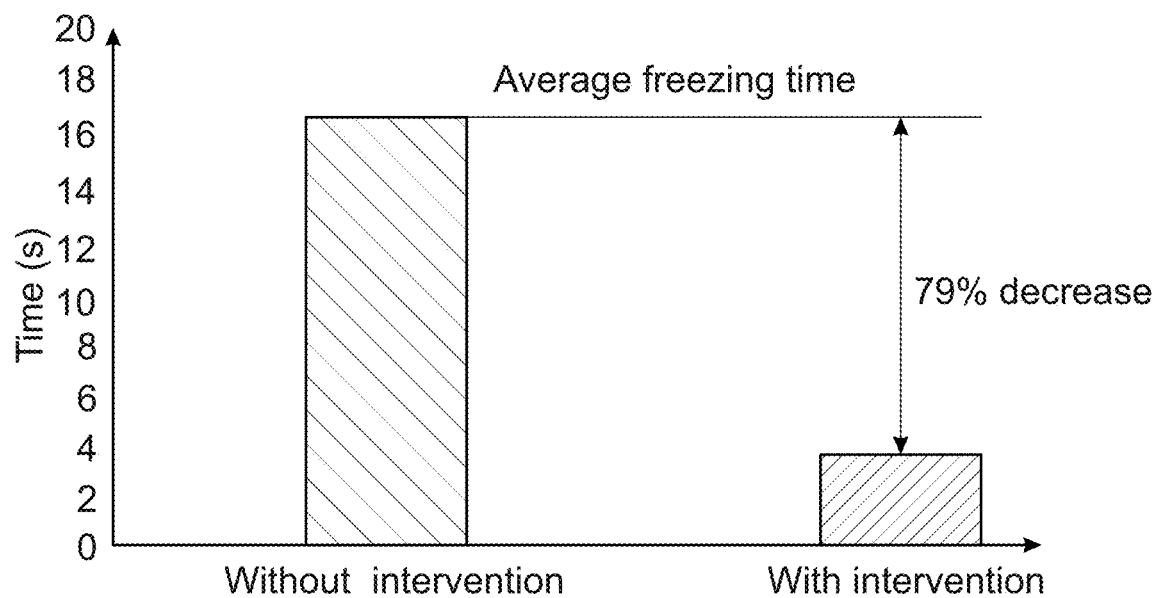
FIGS. 12A-12D: Average freezing time, total time to finish tasks, average stride length, and average step difference between left and right.

FIG. 12A illustrates the average gait freezing duration for eight of the participants of the clinical investigation during the tasks compared between condition A (left) and condition B (right). It can be seen that implementation of the responsive pulse delivery with system 100 decreased the average freezing time by 79%.

Figure 12B:
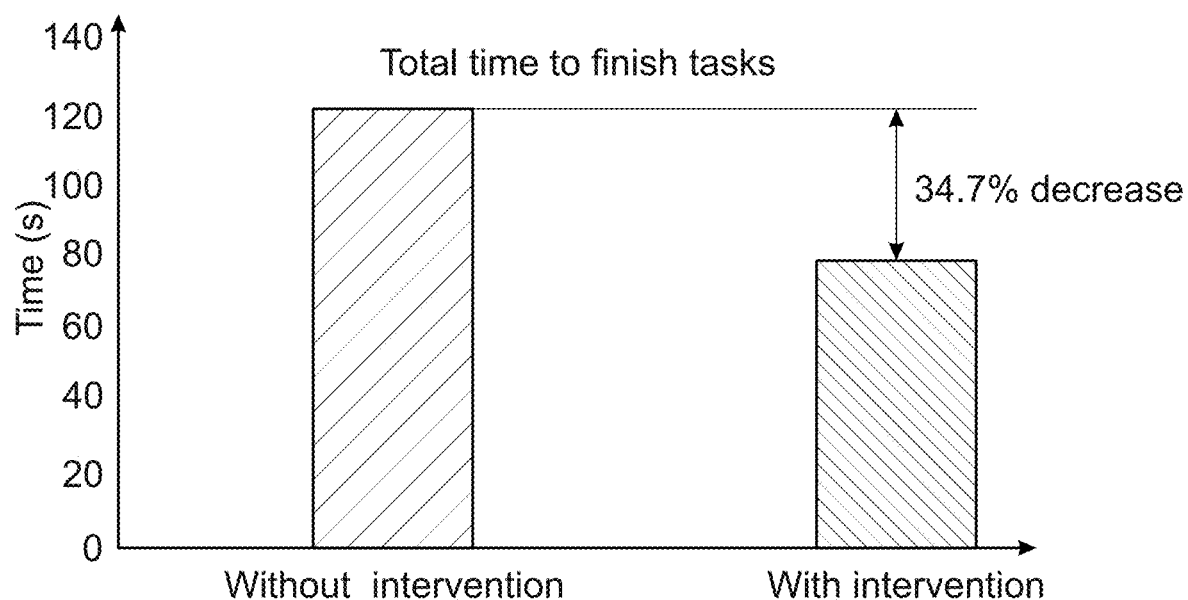

FIG. 12B illustrates the total time to complete the walking tasks for the eight participants comparing condition A (left) and condition B (right). It can be seen that with the responsive pulse delivery the average time taken to complete the walking tasks decreased by 34.75%.

Figure 12C:
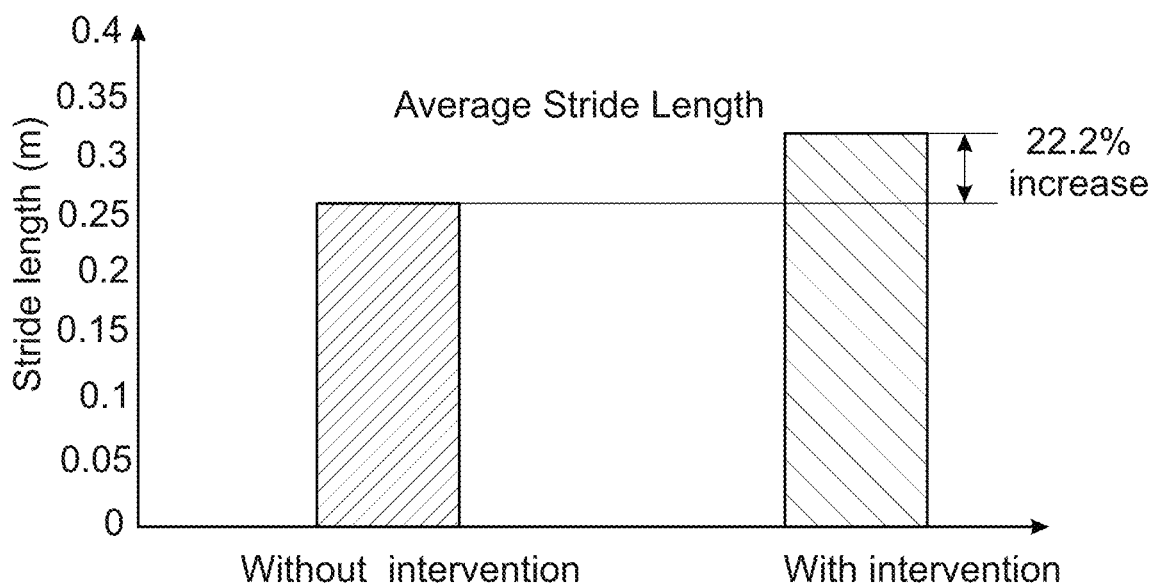

FIG. 12C illustrates the average stride length for the eight participants during the tasks compared between condition A (left) and condition B (right). It can be seen that implementation of the responsive pulse delivery with system 100 increased the average stride length by 22.22%.

Figure 12D:
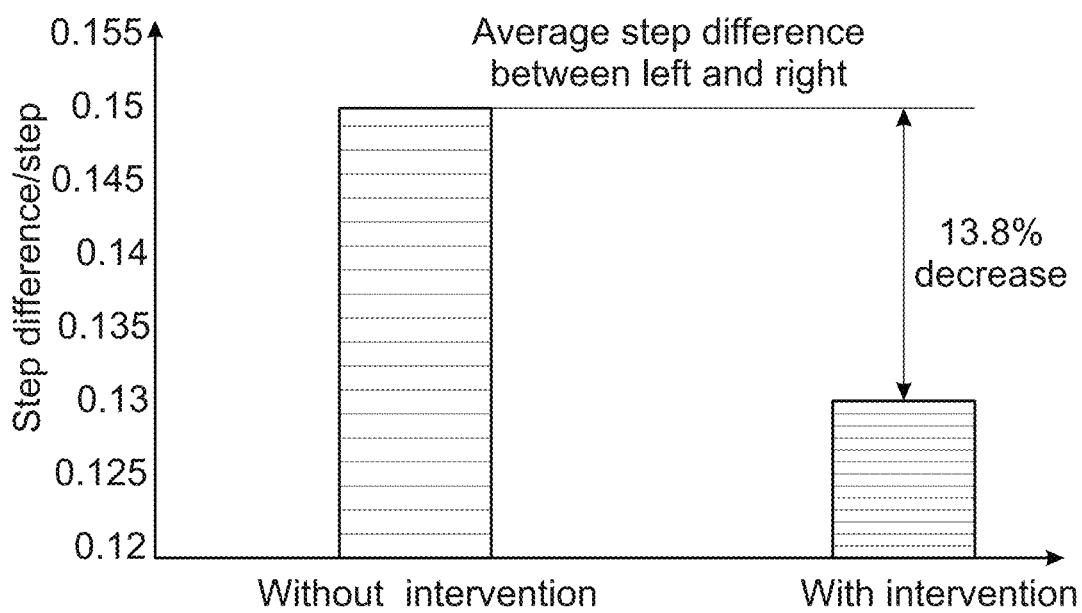

FIG. 12D illustrates the average step symmetry for the eight participants during the tasks compared between condition A (left) and condition B (right). It can be seen that with the responsive pulse delivery the average step symmetry increased by 13.82%.

Figure 13:
FIG. 13: walking map for a participant. As an illustrative example, for one participant
Figure 13:
Figure 13:
Figure 13:

As an illustrative example, for one participant FIG. 13 illustrates a walking map during the walking task under condition A (upper map) compared to a walking map during the walking task under condition B (lower map). It can be seen on the upper map that the participant exhibited severe gait freezing without intervention, which was greatly mitigated by the responsive pulse delivery. The quantitative results for the participant were found to be as follows:

| Gait feature | Condition A | Condition B |
| --- | --- | --- |
| Total time of gait freezing events | >100 s | <3 s |
| Time to conclude walking tests | 385 s | 141 s |
| Stride length | 0.27 m | 0.34 m |

The above table illustrates a 97% decrease in total time of gait freezing events, a 63% reduction in time to conclude the tests, a 20% increase in stride length. There was further found to be an 18% increase in step symmetry.

The system 110 may be configured to perform further methods to improve the suitability of the cue delivery described with reference to FIGS. 3 to 8.

As has been mentioned, the controller 110 may be configured to store movement data 125 associated with the user in memory 112 or on one or more cloud-based systems 240. In addition, the controller may be configured to store additional data indicative of when a FoG or festination event is detected, and the type of cue pattern utilised either in the rhythmic or responsive mode to regulate the gait of the user at a point in time.

The stored movement data 125 and further data may then be utilised by the controller 110 to tailor the determined cue pattern during implementation of method 300, 500 or 700.

During the determination of the cue pattern, the controller 110 may be configured to select a cue pattern historically associated with the most significant improvement in gait quality. The controller 110 may access the historic movement data 125 and determine a gait quality of historic movement data 125 responsive to previous cue patterns provided to the user. The gait quality may be determined in dependence on one or more of the number of FoG or festination events experienced by the user; the duration of said events; duration of time spent continuously walking; time taken to initiate walking; average step frequency; average stride length; and number of fall or near fall events.

The controller 110 may then be configured to select a cue pattern that has resulted in a higher subsequent quality of gait for the user, as determined from the historic movement data 125.

In one example, the historic movement data may comprise movement data from a first time window responsive to the provision of a rhythmic cue at a first pace; and a second time window responsive to the provision of a rhythmic cue at a second pace. The controller 110 may determine that the movement data contained in the first time window is of a higher quality than that contained in the second time window. Consequently, the controller 110 may determine that the provision of a rhythmic cue at the first pace is more beneficial to the user than that provided at the second pace. When determining a suitable cue pattern during future iterations of method 300 or method 500, the controller 110 may determine to provide a cue pattern at the first pace rather than the second pace.

Gait quality of a user may fluctuate throughout the day, for example between periods of the day such as morning or afternoon, or responsive to taking medication. It may be desired to utilise different criteria during implementation of method 300, 500 or 700 during these different periods.

Figure 9:
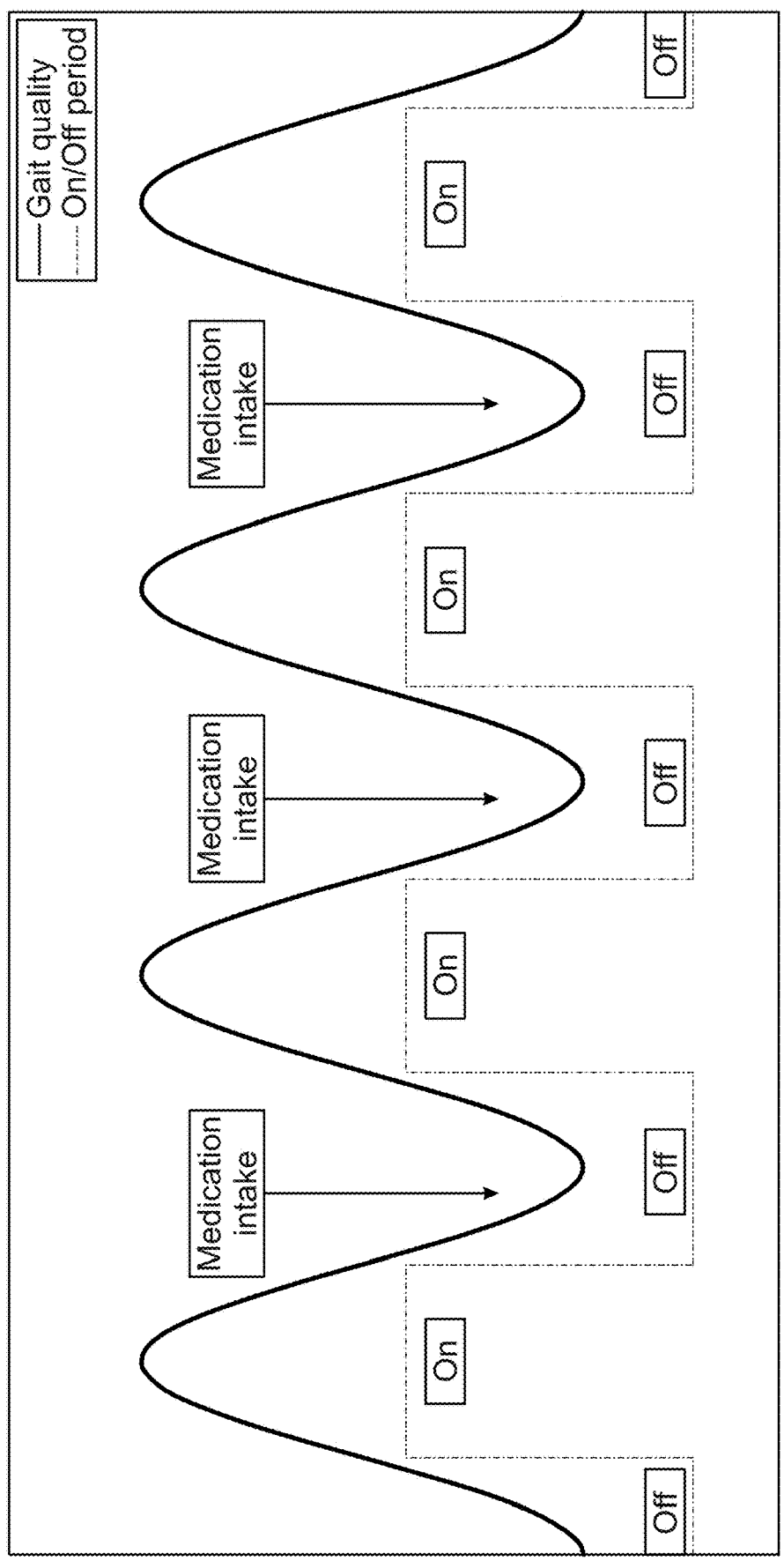
FIG. 9 shows a temporal fluctuation of gait quality and associated classification of time periods that may be utilised according to an embodiment of the invention.

FIG. 9 illustrates an example temporal fluctuation of gait quality corresponding to times of the day at which a user takes medication.

According to some examples of the present invention, the controller 110 may be configured to classify the day into 'on' or 'off' periods in dependence on a determined gait quality of the user. Gait quality may be defined as discussed in relation to the historic movement data 125 above. The controller 110 may determine that on average a particular time period, for example 8 am-11 am, is associated with high gait quality, and classify this time period as a medication 'on' period. Conversely, the controller 110 may classify time periods associated with a low gait quality as medication 'off' periods. An example classification is illustrated superimposed on the gait quality chart shown in FIG. 9.

In other examples of the invention, the user may manually input medication 'on' and 'off' periods to the system 100, for example via the manual controller 150 or another interface communicable with the controller 110.

The different categories of time period, e.g. medication 'on' and 'off' periods, may then be separately associated with different predetermined criteria as discussed in relation to method 300, method 500 and method 700. For example, in method 700 the decision tree may be separately trained on movement data from medication 'on' and medication 'off' periods. In method 500, a different threshold may be assigned during medication 'on' periods and medication 'off' periods. Similarly, the self-learning method described above for selecting the most beneficial cue pattern may be performed separately during medication 'on' and 'off' periods. By separating the method out temporally this way, the determined cues will be better tailored to the user's specific context.

As discussed, the rhythmic and responsive modes may be implemented separately or concurrently, in dependence on the configuration of the system or a specific user input to select a mode of operation. By implementing both rhythmic and responsive cues, the system acts to both prevent debilitating gait events such as FoG by regulating the user's gait before they occur, and rehabilitate the user following the onset of an event. Furthermore, the self-learning aspects of the present invention tailor the specific cues provided to those that bring the most benefit to the gait quality of the user, separately trained for potentially different contextual time periods.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A system for providing targeted cue delivery to regulate a gait of a user comprising:
 a first cue delivery device configured to provide somatosensory stimulation to a first leg of the user;
 a second cue delivery device configured to provide somatosensory stimulation to a second leg of the user;
 one or more inertial sensors configured to output movement data indicative of the gait of the user; and
 a controller configured to:
  receive the movement data from the one or more inertial sensors;
  extract one or more gait characteristics associated with a freezing of gait (FoG) event or a festination event from the movement data;
  in dependence on whether one or more of the gait characteristics meet one or more of a first set of predetermined criteria, determine a cue pattern for each of the first and second cue delivery devices in dependence on the movement data to comprise unilateral stimulation for the first leg by the first cue delivery device,
  output a respective control signal to control each of the first and second cue delivery devices to provide stimulation according to the cue pattern,
  receive further movement data from the one or more inertial sensors;
  detect a step being taken by the first leg in the further movement data; and
  responsive to the step being taken, output a control signal to swap the unilateral stimulation from the first cue delivery device to the second cue delivery device.

2. The system of claim 1, wherein the controller is configured to control the first and second cue delivery devices to cease from providing stimulation or reduce an intensity of the stimulation to the user if one or more of a second set of predetermined criteria are not met.

3. The system of claim 1, wherein the gait characteristics comprise an indication of one or both of a pace of the user and a stride length of a user, and the predetermined criteria comprise one or both of a minimum or maximum pace threshold and a minimum or maximum stride length threshold.

4. The system of claim 1, wherein the controller is configured to determine the cue pattern to be intermittent stimulation by one or both cue delivery devices at a rhythm corresponding to an appropriate pace for the user.

5. The system of claim 4, wherein the controller is configured to determine the appropriate pace for the user in dependence on historic movement data associated with the user.

6. The system of claim 3, wherein the controller is configured to determine one or both of the minimum or maximum pace threshold and the minimum or maximum stride length threshold in dependence on historic movement data associated with the user.

7. The system of claim 1, wherein the movement data comprises a plurality of frequency bands each corresponding to a range of frequency of movement, and the gait characteristics comprise one or more of: a power of a first frequency band of the movement data associated with walking, a power of a second frequency band of the movement data associated with freezing of gait, a ratio of the power of the first and second frequency bands (freeze index), entropy of the movement data, and one or more wavelet transform features of the movement data.

8. The system of claim 1, wherein the controller is configured to associate the extracted gait characteristics with a likelihood of one of a freezing of gait (FoG) event or a festination, and wherein the one or more predetermined criteria comprise a likelihood threshold.

9. The system of claim 8, wherein the controller is configured to:
 apply a decision tree to the extracted gait characteristics; and
 associate the gait characteristics with a likelihood of being indicative of a freezing of gait (FoG) or festination event in dependence thereon.

10. The system of claim 9, wherein the controller is configured to train the decision tree on historic movement data associated with the user indicative of at least one freezing of gait (FoG) or festination event and at least one period of normal gait.

11. The system of claim 1, wherein the controller is configured to identify whether a normal walking pattern has been resumed, and if a normal walking pattern has been resumed, control each of the first and second cue delivery devices to cease providing stimulation.

12. The system of claim 1, wherein the controller is configured to:
receive first historic movement data associated with the provision of a first cue pattern to the user;
receive second historic movement data associated with the provision of a second cue pattern to the user; and
determine the cue pattern to be one of the first cue pattern or the second cue pattern in dependence on a comparison between the first historic movement data and the second historic movement data.

13. The system of claim 1, wherein the controller is configured to:
associate a first time period with a first set of predetermined criteria and a second time period with a second set of predetermined criteria;
determine whether a current time period corresponds to the first time period or the second time period; and
selectively use the predetermined criteria associated with the current time period to determine the cue pattern.

14. The system of claim 1, wherein the somatosensory stimulation comprises a sequence of vibratory pulses according to the cue pattern.

15. A computer-implemented method for providing targeted cue delivery to regulate a gait of a user comprising:
receiving movement data indicative of a gait of a user from one or more inertial sensors;
extracting one or more gait characteristics associated with a freezing of gait (FoG) event or a festination event from the movement data;
in dependence on whether one or more of the gait characteristics meet one or more of a first set of predetermined criteria, determining a first cue pattern for a first cue delivery device and a second cue pattern for a second cue delivery device to comprise unilateral stimulation for the first leg by the first cue delivery device;
providing, with the first cue delivery device, somatosensory stimulation to the first leg of the user according to the first cue pattern;
receiving further movement data from the one or more inertial sensors;
detecting a step being taken by the first leg in the further movement data; and
responsive to the step being taken, swapping the unilateral stimulation from the first cue delivery device to the second cue delivery device; and
providing, with the second cue delivery device, somatosensory stimulation to a second leg of the user according to the second cue pattern.

16. The method of claim 15, comprising determining one or both of the first and second cue patterns to be intermittent stimulation at a rhythm corresponding to an appropriate pace for the user.

17. The method of claim 15, comprising associating the extracted gait characteristics with a likelihood of one of a freezing of gait (FOG) event or a festination, and wherein the one or more predetermined criteria comprise a likelihood threshold.

18. The method of claim 17, comprising:
applying a decision tree to the extracted gait characteristics; and
associating the gait characteristics with a likelihood of being indicative of a freezing of gait (FoG) or festination event in dependence thereon.

19. A non-transitory computer readable medium comprising computer readable instruction that, when executed by a processor, causes performance of the method of claim 15.

* * * * *